(12) United States Patent
Fischer

(10) Patent No.: US 9,821,321 B2
(45) Date of Patent: Nov. 21, 2017

(54) LOCALIZED DESALTING SYSTEMS AND METHODS

(71) Applicant: Abbott Laboratories, Abbott Park, IL (US)

(72) Inventor: Andrew Fischer, Euless, TX (US)

(73) Assignee: ABBOTT LABORATORIES, Abbott Park, IL (US)

(*) Notice: Subject to any disclaimer, the term of this patent is extended or adjusted under 35 U.S.C. 154(b) by 0 days.

(21) Appl. No.: 15/339,023

(22) Filed: Oct. 31, 2016

(65) Prior Publication Data

US 2017/0043355 A1    Feb. 16, 2017

Related U.S. Application Data

(63) Continuation of application No. 14/055,588, filed on Oct. 16, 2013, now Pat. No. 9,488,614.

(60) Provisional application No. 61/714,658, filed on Oct. 16, 2012.

(51) Int. Cl.
| | |
|---|---|
| *G01N 27/414* | (2006.01) |
| *B03C 5/00* | (2006.01) |
| *G01N 27/327* | (2006.01) |
| *G01N 27/447* | (2006.01) |
| *G01N 33/543* | (2006.01) |

(52) U.S. Cl.
CPC ......... *B03C 5/005* (2013.01); *G01N 27/3275* (2013.01); *G01N 27/4145* (2013.01); *G01N 27/4146* (2013.01); *G01N 27/44791* (2013.01); *G01N 33/5438* (2013.01); *B01L 2200/0631* (2013.01); *B01L 2200/0694* (2013.01); *B01L 2200/10* (2013.01); *B01L 2300/0636* (2013.01); *B01L 2400/0415* (2013.01)

(58) Field of Classification Search
CPC ........... G01N 27/4145; G01N 27/3275; G01N 27/4146; B01L 2200/0631; B01L 2200/0694; B01L 2200/10; B01L 2300/0636; B01L 2400/0415
See application file for complete search history.

(56) References Cited

U.S. PATENT DOCUMENTS

| | | |
|---|---|---|
| 5,568,499 A | 10/1996 | Lear |
| 5,654,579 A | 8/1997 | Bauer et al. |
| 6,284,117 B1 | 9/2001 | Smolko et al. |

(Continued)

FOREIGN PATENT DOCUMENTS

| | | |
|---|---|---|
| CA | 2646465 | 9/2007 |
| CA | 2655340 | 5/2008 |

(Continued)

OTHER PUBLICATIONS

Gao et al., "Enhanced Sensing of Nucleic Acids with Silicon Nanowire Field Effect Transistor Biosensors," Nano Letters, vol. 12, p. 5262, 2012, 7 pages.

(Continued)

*Primary Examiner* — Susan D Leong
(74) *Attorney, Agent, or Firm* — Hanley, Flight & Zimmerman, LLC

(57) ABSTRACT

Example apparatus, systems and methods to desalt a sample are disclosed. An example method includes introducing a sample into an apparatus, in which the apparatus includes a sensor coupled to a substrate and an electrode. The example method also includes applying, via the electrode, an electric potential to the sample to redistribute ions in the sample relative to the sensor.

18 Claims, 19 Drawing Sheets

(56) References Cited

U.S. PATENT DOCUMENTS

| | | |
|---|---|---|
| 6,558,973 B2 | 5/2003 | Johnson et al. |
| 6,946,703 B2 | 9/2005 | Ryu et al. |
| 7,009,224 B2 | 3/2006 | Johnson et al. |
| 7,328,153 B2 | 2/2008 | Wells et al. |
| 7,374,991 B2 | 5/2008 | Ryu et al. |
| 7,385,231 B2 | 6/2008 | Fujimoto et al. |
| 7,385,234 B2 | 6/2008 | Gopalakrishnan et al. |
| 7,476,893 B2 | 1/2009 | Yang et al. |
| 7,898,005 B2 | 3/2011 | Yang et al. |
| 8,377,280 B2 | 2/2013 | Johnson |
| 2002/0110946 A1 | 8/2002 | Johnson et al. |
| 2003/0215971 A1 | 11/2003 | Johnson et al. |
| 2004/0207002 A1 | 10/2004 | Ryu et al. |
| 2005/0034990 A1 | 2/2005 | Crooks et al. |
| 2005/0191683 A1 | 9/2005 | Yoo et al. |
| 2006/0180853 A1 | 8/2006 | Ryu et al. |
| 2006/0197118 A1 | 9/2006 | Migliorato et al. |
| 2006/0244047 A1 | 11/2006 | Gopalakrishnan et al. |
| 2006/0284230 A1 | 12/2006 | Yang et al. |
| 2007/0049047 A1 | 3/2007 | Fujimoto et al. |
| 2007/0178507 A1 | 8/2007 | Wu et al. |
| 2007/0246362 A1 | 10/2007 | Luedke |
| 2008/0035494 A1 | 2/2008 | Gomez et al. |
| 2008/0308816 A1 | 12/2008 | Miller et al. |
| 2009/0142825 A1 | 6/2009 | Murray et al. |
| 2009/0283751 A1 | 11/2009 | Yang et al. |
| 2010/0025660 A1 | 2/2010 | Jain et al. |
| 2010/0072976 A1 | 3/2010 | Sheu et al. |
| 2010/0087013 A1 | 4/2010 | Lieber et al. |
| 2010/0140096 A1 | 6/2010 | Yang et al. |
| 2010/0152057 A1 | 6/2010 | Lieber et al. |
| 2010/0216256 A1 | 8/2010 | Cheng et al. |
| 2010/0248284 A1 | 9/2010 | Chen et al. |
| 2010/0252434 A1 | 10/2010 | Roy |
| 2010/0282617 A1 | 11/2010 | Rothberg et al. |
| 2010/0297608 A1 | 11/2010 | Stern et al. |
| 2010/0327874 A1 | 12/2010 | Liu et al. |
| 2011/0086352 A1 | 4/2011 | Bashir et al. |
| 2011/0198225 A1 | 8/2011 | Kim et al. |
| 2011/0291673 A1 | 12/2011 | Shibata et al. |
| 2012/0021918 A1 | 1/2012 | Bashir et al. |
| 2014/0054651 A1 | 2/2014 | Bashir et al. |
| 2014/0106338 A1 | 4/2014 | Fischer |

FOREIGN PATENT DOCUMENTS

| | | |
|---|---|---|
| CN | 102159303 | 8/2011 |
| EP | 2035584 | 1/2011 |
| WO | 2004/009849 | 1/2004 |
| WO | 2005/032717 | 4/2005 |
| WO | 2006/095252 | 9/2006 |
| WO | 2007/084076 | 7/2007 |
| WO | 2008/039579 | 4/2008 |
| WO | 2008/043040 | 4/2008 |
| WO | 2008/127314 | 10/2008 |
| WO | 2009/070426 | 6/2009 |
| WO | 2010/011760 | 1/2010 |
| WO | 2010/016807 | 2/2010 |
| WO | 2010/030057 | 3/2010 |
| WO | 2010/044932 A2 | 4/2010 |
| WO | 2010/044932 A3 | 4/2010 |
| WO | 2010/044932 A9 | 4/2010 |
| WO | 2011/014946 | 2/2011 |
| WO | 2012/078340 | 6/2012 |
| WO | 2013/016486 | 1/2013 |
| WO | 2013/173754 | 11/2013 |

OTHER PUBLICATIONS

Delgado et al., "Measurement and Interpretation of Electrokinetic Phenomena," Pure and Applied Chemistry, vol. 77, p. 1753, 2005, 31 pages.

Dorvel et al., "Vapor-Phase Deposition of Monofunctional Alkoxysilanes for Sub-Nanometer-Level Biointerfacing on Silicon Oxide Surfaces," Advanced Functional Materials, vol. 20, p. 87, 2010, 11 pages.

Dorvel et al., "Effect of Biointerfacing Linker Chemistries on the Sensitivity of Silicon Nanowires for Protein Detection," Analytical Chemistry, vol. 85, p. 9493, 2013, 8 pages.

Honig et al., "Classical Electrostatics in Biology and Chemistry," Science, vol. 268, p. 1144, May 26, 1995, 7 pages.

Hindson et al., "High-Throughput Droplet Digital PCR System for Absolute Quantitation of DNA Copy Number," Analytical Chemistry, vol. 83, p. 8604, 2011, 7 pages.

Dorvel et al., "Silicon Nanowires with High-k Hafnium Oxide Dielectrics for Sensitive Detection of Small Nucleic Acid Oligomers," ACS Nano, vol. 6, pp. 6150-6164, 2012, 15 pages.

Reddy, Jr. et al., "High-k Dielectric Al2O3 Nanowire and Nanoplate Field Effect Sensors for Improved pH Sensing," Biomed Microdevices, vol. 2, pp. 335-344, 2011, 11 pages.

Salm et al., "Ultra-localized Thermal Reactions in Sub-Nanoliter Droplets-in-Air," Proceedings of the National Academy of Sciences Early Edition, pp. 3310-3315, 2013, 6 pages.

Stern et al., "Label-free Biomarker Detection from Whole Blood," Nature Nanotechnology, Feb. 2010, vol. 5, 11 pages.

Ebrahimi et al. "Nanotextured Superhydrophobic Electrodes Enable Detection of Attomolar-scale DNA Concentration within a Droplet by Non-faradaic Impedance Spectroscopy," Lab on a Chip, vol. 13, p. 4248, 2013, 9 pages.

Patolsky et al., "Electrical Detection of Single Viruses," Proceedings of the National Academy of Sciences, vol. 101, p. 14017, 2004, 6 pages.

Ishikawa et al., Label-free, Electrical Detection of the SARS Virus N-Protein with Nanowire Biosensors Utilizing Antibody Mimics as Capture Probes, ACS Nano, vol. 3, p. 1219, 2009, 6 pages.

Kulkarni et al., "Detection Beyond the Debye Screening Length in a High-Frequency Nanoelectronic Biosensor," Nano Letters, vol. 12, p. 719, 2012, 5 pages.

Zhang et al., "Label-free Direct Detection of MiRNAs with Silicon Nanowire Biosensors," Biosensors and Bioelectronics. vol. 24, p. 2504, 2009, 5 pages.

Zhang et al., "Porous Dendritic Plantinum Nanotubes with Extremely High Activity and Stability for Oxygen Reduction Reaction," Scientific Reports., vol. 3, Mar. 2013, 8 pages.

Zheng et al., "Multiplexed Electrical Detection of Cancer Markers with Nanowire Sensor Arrays," Nature Biotechnolgy, vol. 23, p. 1294, 2005, 9 pages.

Zhang et al., "DNA Sensing by Silicon Nanowire: Charge Layer Distance Dependence," Nano Letters, vol. 8, pp. 1066-1070, 2008, 5 pages.

Heer et al, "CMOS Microelectrode Arrary for the Monitoring of Electrogenic Cells," Biosensors & Bioelectronics, vol. 20, p. 358, 2004, 9 pages.

Borukhov et al., "Steric Effects in Electrolytes: A Modified Poisson-Boltzmann Equation," Physical Review Letters, vol. 79, p. 435, 1997, 4 pages.

Rothberg et al., "An Integrated Semiconductor Device Enabling Non-optical Genome Sequencing," Nature, vol. 475., No. 7356, pp. 348-352, Jul. 2011, 6 pages.

Go et al., "Coupled Heterogeneous Nanowire-Nanoplate Planar Transistor Sensors for Giant (>10V/pH) Nernst Response," ACS Nano, vol. 7, pp. 5972-5979, 2012, 8 pages.

Lee et al., "Electrode Reactions and Adsorption/desorption Performance Related to the Applied Potential in a Capacitive Deionization Process," Desalination, vol. 258, pp. 159-163, 2010, 5 pages.

Ahn et al., "Double-Gate Nanowire Field Effect Transistor for a Biosensor," Nano Letters, vol. 10, p. 2934, 2010, 5 pages.

Ahn et al., "A pH Sensor with a Double-gate Silicon Nanowire Field-effect Transistor," Applied Physics Letters, vol. 102, p. 083701, 2013, 6 pages.

Kang et al., Development of an Equivalent Circuit Model for Electrochemical Double Layer Capacitors (EDLCs) with Distinct Electrolytes, Eltrochimica Acta, vol. 115, pp. 587-598, 2014, 12 pages.

Kim et al., "Direct Label-free Electrical Immunodetection in Human Serum Using a Flow-through-apparatus Approach with

(56) References Cited

OTHER PUBLICATIONS

Intergrated Field-effect Transistors," Biosensors and Bioelectronics, vol. 25, No. 7, pp. 1767-1773, 2009, 7 pages.
Zhu et al., "An On-demand Microfluidic Hydrogen Generator with Self-regulated Gas Generation and Self-circulated Reactant Exchange with a Rechargeable Reservoir," Microfluidics and Nanofluidics, vol. 11, No. 5, pp. 569-578, 2011, 10 pages.
Andelman, "Flow through Capacitor Basics," Separation and Purification Technology. vol. 80, pp. 262-269, 2011, 8 pages.
Gouy, "Sur La Constitution De La Charge Electrique a La Surface D'un Electrolyte", Journal de Physique Théorique et Appliquée, vol. 9, p. 457, 1910, 12 pages.
Sorensen et al., "Screening model for nanowire surface-charge sensors in liquid," Applied Physics Letters, vol. 91, p. 102105, 2007, 4 pages.
Kilic et al., "Steric Effects in the Dynamics of Electrolytes at Large Applied Voltages. II. Modified Poisson-Nernst-Planck Equations," Physical Review E, vol. 75, p. 021503, Feb. 2007, 11 pages.
Nair et al., "Design Considerations of Silicon Nanowire Biosensors," IEEE Transactions on Electron Devices, vol. 54, No. 12, pp. 3400-3408, 2007, 9 pages.
Demirer and C.H. Hidrovo, "Laser-induced Fluorescence Visualization of Ion Transport in a Pseudo-porous Capacitive Deionization Microstructure," Microfluidics and Nanofluidics, vol. 16, pp. 109-122, Jul. 2013, 14 pages.
Bergveld, "Thirty Years of ISFETOLOGY, What Happened in the Past 30 years and What May Happen in the Next 30 years," Sensors and Actuators B: Chemical, vol. 88, No. 1, accepted Aug. 15, 2002, 20 pages.
Bergveld, "The Development and Application of FET-based biosensors." Biosensors 2, pp. 15-33, 1986, 19 pages.
Nair et al., "Performance Limits of Nanobiosensors," Applied Physics Letters, vol. 88, No. 23, p. 233120, 2006, 4 pages.
Jayashree et al., "Characterization and Application of Electrodeposited Pt, Pt/Pd, and Pd Catalyst Structures for Direct Formic Acid Micro Fuel Cells," Electrochimica Acta, vol. 50, No. 24, pp. 4674-4682, 2005, 9 pages.
Elnathan et al., "Biorecognition Layer Engineering: Overcoming Screening Limitations of Nanowire-Based FET Devices," Nano Letters. vol. 12, pp. 5245-5254, 2012, 10 pages.
Chen et al., "Contacting versus Insulated Gate Electrode for Si Nanoribbon Field-Effect Sensors Operating in Electrolyte," Analytical Chemistry, vol. 83, pp. 9546-9551, 2011, 6 pages.
Purushothaman et al., "Protons and single nucleotide polymorphism detection: A simple use for the Ion Sensitive Field Effect Transistor," Sensors and Actuators B: Chemical, vol. 114, pp. 964-968, 2005, 5 pages.
Welgemoed et al., "Capacitive Deionization Technology: An alternative desalination solution," Desalination, vol. 183, pp. 327-340, 2005, 14 pages.
Barragan et al., "Effect of an AC perturbation on a desalination electrodialysis process," Desalination, vol. 142, 235-244, 2002, 10 pages.
Guan et al., "Field-effect Reconfigurable Nanofluidic Ionic Diodes," Nature Communications, vol. 2, p. 526., 2011, 8 pages.
Ye et al., "Self-assembled synthesis of SERS-active silver dendrites and photoluminescence properties of a thin porous silicon layer," Electrochemical Commununications, vol. 10, pp. 625-629, 2008, 5 pages.

Cui et al., "Nanowire Nanosensors for Highly Sensitive and Selective Detection of Biological and Chemical Species," Science, vol. 293, No. 5333, pp. 1289-1292, Aug. 2001, 5 pages.
Huh, et al., "Advanced cleanup process of the free-flow microfluidic device for protein analysis," Ultramicroscopy, vol. 108, pp. 1365-1370, 2008, 6 pages.
Bunimovich et al., "Quantitative Real-Time Measurements of DNA Hybridization with Alkylated Nonoxidized Silicon Nanowires in Electrolyte Solution," Journal of American Chemical Society, vol. 128, pp. 16323-16331, 2006, 9 pages.
Huang et al., "Metal-Assisted Chemical Etching of Silicon: A Review," Advanced Materials, vol. 23, pp. 285-308, 2011, 24 pages.
International Searching Authority, "International Search Report and Written Opinion", issued for International Patent Application No. PCT/US2013/065233, dated Jan. 28, 2014, 15 pages.
Daguji, H. et al. "Ion Transport in Nanofluidic Channels", Nano Letters, Jan. 2004, 6 pages.
Nishguchi et al. "Si Nanowire Ion-sensitive Field-Effect Transistors With a Shared Floating Gate", Applied Physics Letters, vol. 94, Issue 16, 2009, 3 pages.
Ah et al., "Electronic Detection of Biomarkers by Si Field-Effect Transistor from Undiluted Sample Solutions With High Ionic Strengths", Bulletin of Korean Chemical Society, vol. 31, No. 6, Mar. 29, 2010, 7 pages.
Uno et al., "Peptide-Nucleic Acid-Modified Ion-Sensitive Field-Effect Transistor-Based Biosensor for Direct Detection of DNA Hybridization", Analytical Chemistry, vol. 79, No. 1, Jan. 1, 2007, 8 pages.
Fernandes et al., "SPICE Macro Model of Silicon-On-Insulator-Field-Effect-Transistor-Based Biological Sensors", Sensors and Actuators: B Chemical, Oct. 3, 2011, 8 pages.
Von Guggenberg, P.A., "Voltage-Controlled Double Layer", Proceedings of the 1993 Conference on Electrical Insulation and Dielectric Phenomena, Dec. 1, 1993, 6 pages.
Jagota, Anand, "CNT-Based Sensors", http://www.lehigh.edu/~anj6/CNT basedSensor.html, retrieved on Feb. 17, 2014, 3 pages.
Stern, Eric, "Importance of the Debye Screening Length on Nanowire Field Effect Transistor Sensors", Nano Letters, vol. 7, No. 11, 2007, 5 pages.
Heitzinger et al., "Calculation of Fluctuations in Boundary Layers of Nanowire Field-Effect Biosensors", Journal of Computational and Theoretical Nanosicence, vol. 7, 1-7, 2010, 7 pages.
Liu et al., "Overcoming the Screening-Induced Performance Limits of Nanowire Biosensors: A Simulation Study on the Effect of Electro-Diffusion Flow", The Institute of Electrical and Electronics Engineers Inc., International Electron Devices Meeting, 2008, 4 pages.
International Searching Authority, "International Preliminary Report on Patentability," issued for International Patent Application No. PCT/US2013/065233, dated Apr. 30, 2015, 11 pages.
State Intellectual Property Office of China, "First Office Action," issued in connection with Chinese Patent Application No. 201380065880.4, dated Oct. 8, 2016, 22 pages.
United States Patent and Trademark Office, "Notice of Allowance and Fee(s) Due," issued in connection with U.S. Appl. No. 14/055,588, dated Jul. 12, 2016, 18 pages.
United States Patent and Trademark Office, "Restriction Requirement," issued in connection with U.S. Appl. No. 14/055,588, dated Apr. 7, 2016, 8 pages.
State Intellectual Property Office of China, "Second Office Action," issued in connection with Chinese Patent Application No. 201380065880.4, dated Jun. 1, 2017, 18 pages.

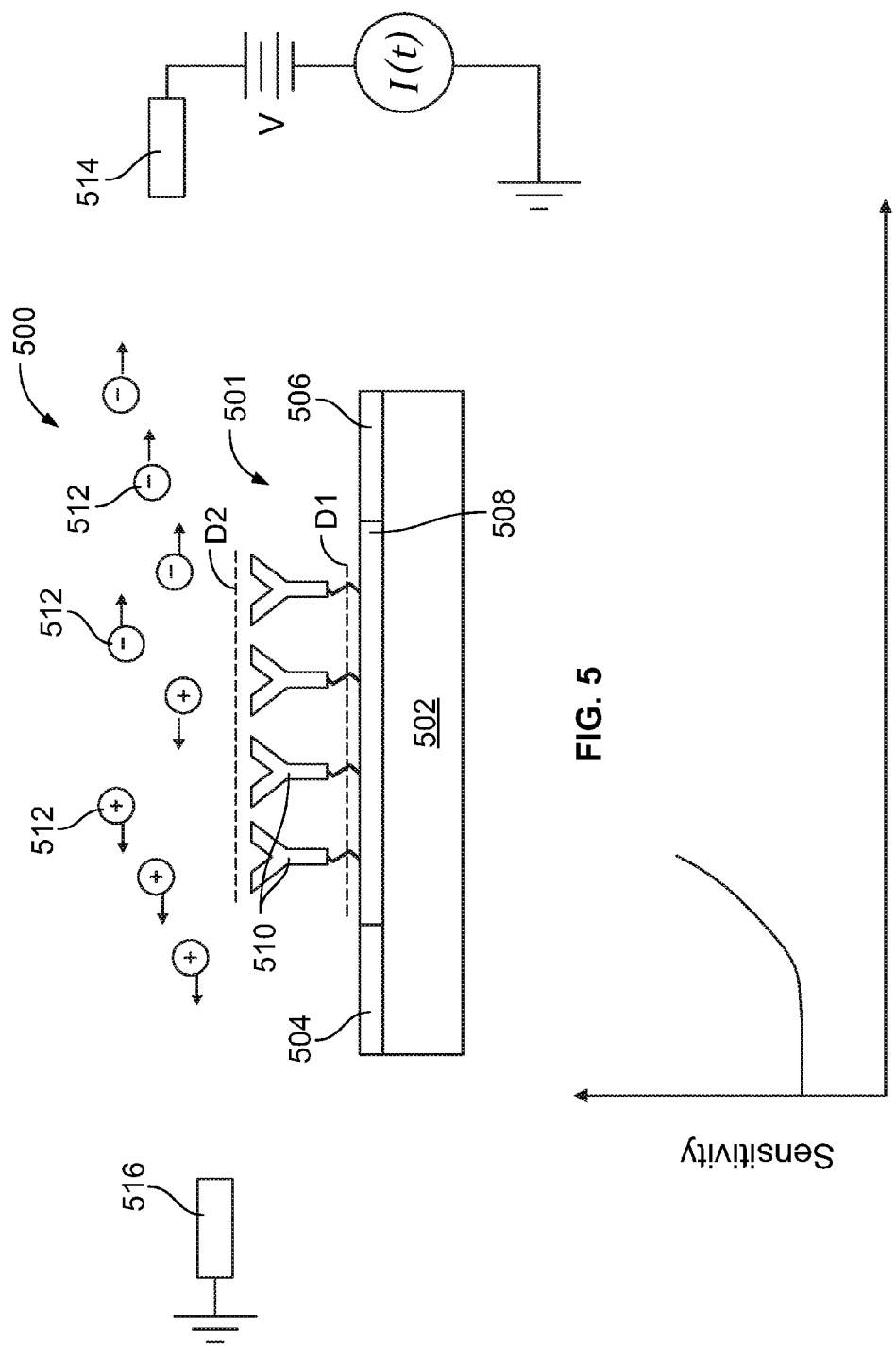

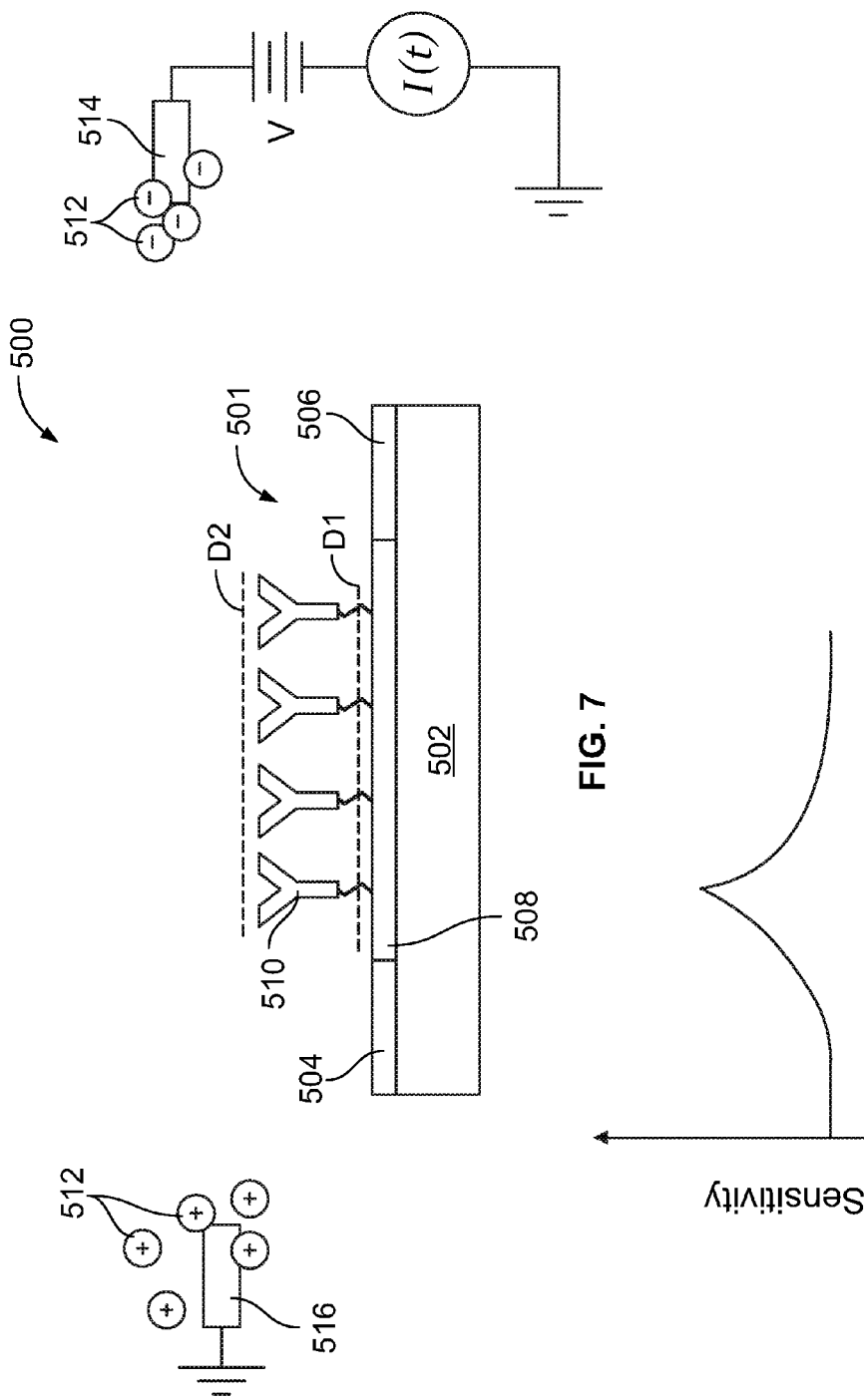

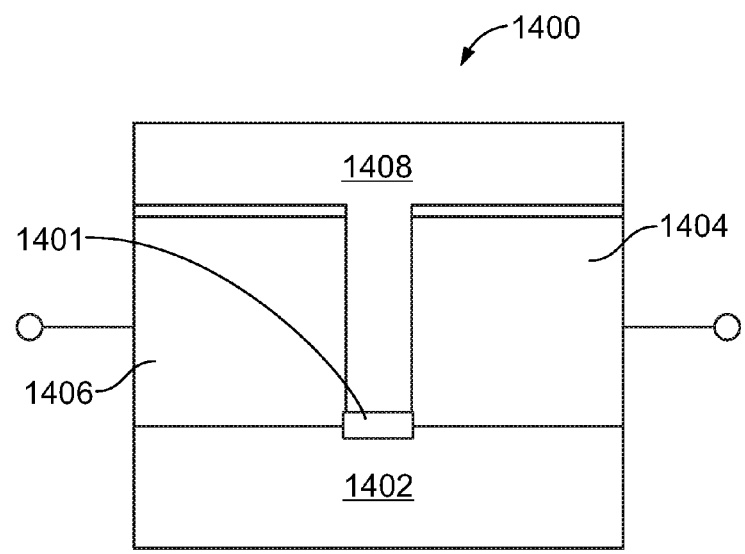
FIG. 14
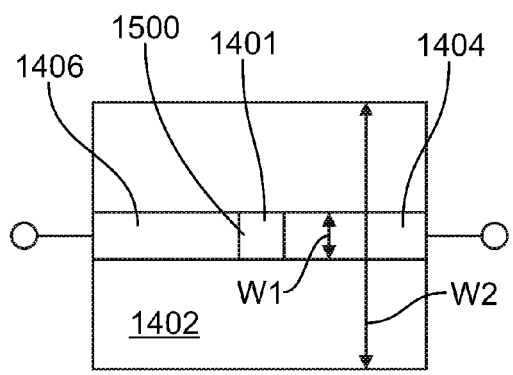    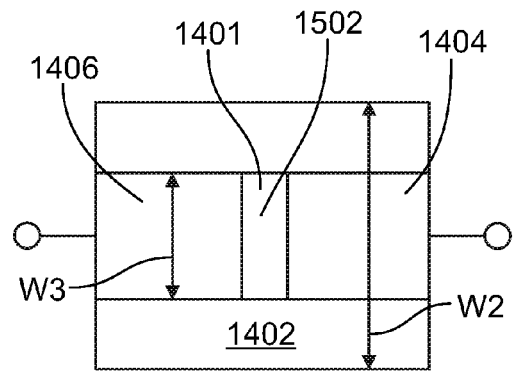
FIG. 15A                FIG. 15B

LOCALIZED DESALTING SYSTEMS AND METHODS

RELATED APPLICATIONS

This patent arises from a continuation of U.S. application Ser. No. 14/055,588, titled "LOCALIZED DESALTING SYSTEMS AND METHODS," filed on Oct. 16, 2013, which claims priority to U.S. Provisional Application No. 61/714,658, titled "LOCALIZED DESALTING SYSTEMS AND METHODS," and filed on Oct. 16, 2012. U.S. application Ser. No. 14/055,588 and U.S. Provisional Application No. 61/714,658 are incorporated herein by this reference in their entireties.

FIELD OF THE DISCLOSURE

The present disclosure relates generally to molecular detection systems and, more particularly, to apparatus, systems and methods for increasing sensitivity in molecular detection systems.

BACKGROUND

Nanostructured sensors are widely used in the medical and chemical industries to measure the presence and/or concentration of a desired compound in a sample such as an analyte or other molecules. Nanostructured sensors typically require only a very small sample and are typically very sensitive. Common nanostructured sensors use electrical based detection such as, for example, field-effect transistors (FET). Typically, these sensors include semiconducting material located between two electrodes, whereby the semiconducting material is functionalized with a binding agent such as an antibody or aptamer. Binding a compound of interest or target molecule to the binding agent on the surface of the sensor induces electrical property changes through the semiconducting material and, thus, can be measured and correlated to the concentration of the compound within the sample. When seeking the concentration of a biological sample or biomolecule such as, for example, in medical and clinical analyzers, these nanostructured sensors are often referred to as biosensors. Biosensors are commonly used to measure the concentration of an analyte such as an antibody, an antigen, etc. in a sample fluid such as serum, blood, or urine.

Salt or ions build up at the biosensors and reduce sensitivity. Some example methods of desalting or deionizing samples utilize offline treatments with an ultrafiltration membrane. These methods suffer in that analytes that are present in low concentration may be lost during the filtration steps. Other example methods utilize desalting solutions such as dialysis, gel filtration columns, and on-chip membranes. These methods also suffer from drawbacks including potential loss of low-abundance proteins, increased cost, and increased complexity.

BRIEF DESCRIPTION OF THE DRAWINGS

FIG. 5 is an illustration of another example system or apparatus for desalting samples having two electrodes.

FIG. 6 is a graph of sensitivity versus time for the example system of FIG. 5.

FIG. 7 shows the example system or apparatus of FIG. 5 after operation for a period of time.

FIG. 8 is a graph of sensitivity versus time for the example system or apparatus of FIGS. 5 and 7.

FIG. 14 illustrates an example system or apparatus for desalting samples having example electrodes with increased height.

FIG. 15A is a top view of the example system or apparatus of FIG. 14 including electrodes having a first width.

FIG. 15B is a top view of the example system or apparatus of FIG. 14 including electrodes having a second width.

DETAILED DESCRIPTION

Figure 1:
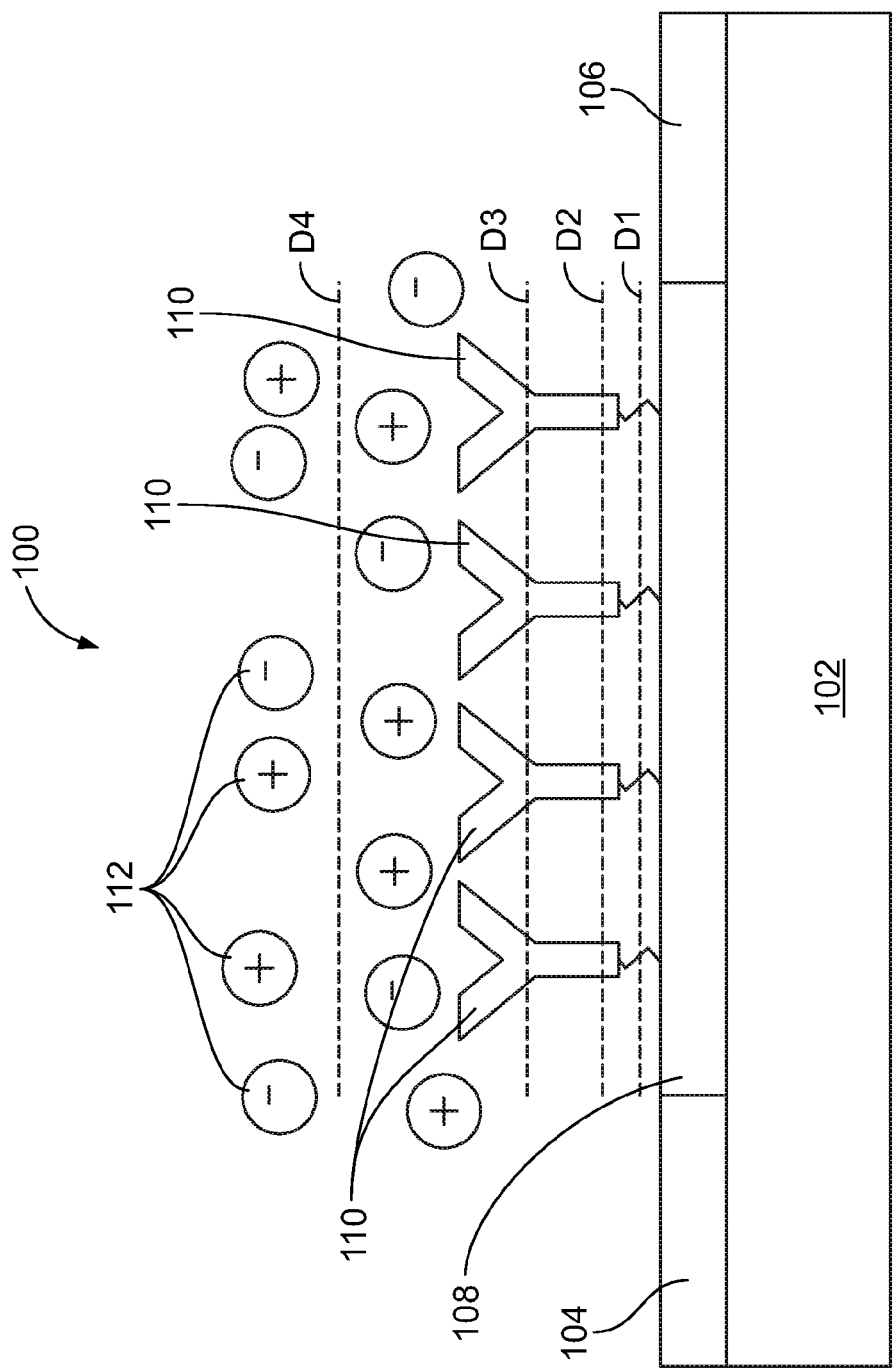
FIG. 1 shows a side view of an example nanostructured sensor for measuring and detecting a compound in a sample.

Although this specification discloses example apparatus and systems including, among other components, software and/or firmware executed on hardware, it should be noted that such apparatus and systems are merely illustrative and should not be considered as limiting. For example, it is contemplated that any or all of these hardware, software, and firmware components could be embodied exclusively in hardware, exclusively in software, or in any combination of hardware and software. Accordingly, while the following describes example apparatus and systems, persons of ordinary skill in the art will readily appreciate that the examples provided are not the only way to implement such apparatus and systems.

Some nanostructured sensors (e.g., biosensors) use electrical based detection such as, for example, field-effect transistors (FET), to detect a concentration of a desired compound in a sample. Such nanostructured sensors operate by measuring a change in an electrical property that is modified upon binding or proximity of a molecule (e.g., a compound, an analyte, an antibody, an antigen, an aptamer and/or other substance). A surface of the sensor is functionalized with a binding agent (e.g., a protein, a cell, a virus, a nucleic acid, an antigen, an antibody, a matrix protein, an enzyme, a coenzyme, a ligand, an aptamer, a receptor, etc.) to specifically bind with a particular molecule (e.g., analyte) known as an analyte of interest or target molecule. If an ionic concentration within the sample solution is low, the electrical properties of the surface of the sensor may change upon the binding of the analyte and, thus, the sensor can detect the analyte of interest. Specifically, the analyte of interest has a net charge associated with it, and upon binding, the charge of the analyte modulates the charge density within a component of the sensor such as, for example, a semiconductive gate electrode of an FET. This modulation of charge density on the gate electrode of the FET is characterized by a change in one or more of a resistance, a current, a voltage, a capacitance, an impedance, etc.

In some examples, the gate electrode in the FET sensors includes a nanowire. A nanowire is a semiconductive structure that may include, for example, nanorod(s), nanotube(s), nanoribbon(s), etc. Furthermore, example nanowires have a large aspect ratio (e.g., length to width). In some examples, nanowire sensors include semiconducting material located between the two electrodes (e.g., gate electrodes), whereby the semiconducting material is functionalized with a binding agent (e.g., antibody, aptamer, etc.). Also, in some examples, the gate electrodes are fabricated from materials including, for example, a semiconductive material such as, for example, silicon. In some examples, the semiconductive material is doped to be an n-type semiconductor and, in some examples, the semiconductive material is doped to be a p-type semicondictor.

Due to the level of sensitivity, nanowire sensors are able to advantageously measure concentrations of an analyte of interest in small samples. For example, when measuring biological material, binding of an analyte of interest to the surface of the sensor induces electrical property changes through the semiconducting material, as described above. The electrical property is measured and correlated to the concentration of the analyte within the sample, and this detection can occur with very small sample sizes.

Furthermore, because of the scale, nanowire sensors are sensitive and have low (atto-molar) detection limits in low ionic strength solutions. However, the sensitivity of nanowire sensors is limited by charge screening at high ionic strengths. In other words, these nanostructured sensors are affected by ionic charges (e.g., salt) in the sample fluid that can distort the detection operations.

A Debye length is defined as the distance from a sensor surface at which ions (e.g., salt) in a solution effectively screen an electrical response induced by an analyte. Solutions with a high ionic strength have a small Debye length because the high number of ions negate charge influences at long distances. Samples are to be deionized (e.g., desalted) to maintain the low detection limits of analytes in physiological solutions. For example, an ionic strength of a physiological solution that is around 200 millimolar (mM) equates to a Debye length of around 1 nanometer (nm). Because a size of antibodies is about 5 nm to about 10 nm, the analyte binding events would be difficult to detect and may go undetected.

An example apparatus disclosed herein includes a substrate, a sensor coupled to the substrate where the sensor is to detect an analyte in a sample, and a first electrode to create an electric potential and reposition ions in the sample relative to a surface of the sensor.

In some examples, the sample is a raw sample and does not contain a buffer solution of low ionic concentration. In some examples, the sensor comprises a field-effect transistor having a gate. In some examples, the gate is functionalized with a binding agent to interact with the analyte. In some such examples, the gate comprises a nanostructure. In other examples, the first electrode is to reposition ions in the sample closer to the gate of the field-effect transistor.

In some examples, the first electrode is substantially coplanar with the sensor on the substrate.

In some examples, the apparatus includes a second electrode disposed on the substrate. In some such examples, the sensor is located between the first electrode and the second electrode. In some examples, the first electrode is to provide a positive electric voltage or a negative electric voltage and the second electrode is a ground electrode. In other examples, the first electrode is to provide a positive electric voltage and the second electrode is to provide a negative electric voltage. In still other examples, both the first and second electrodes are to provide a positive electric voltage or both the first and second electrodes are to provide a negative electric voltage. In some examples, the magnitude of the voltage differs between the first and second electrodes.

In some examples, the apparatus includes a third electrode and a fourth electrode disposed on the substrate. In some such examples, the first electrode, the second electrode, the third electrode and the fourth electrode are disposed on each of four sides around the sensor.

In some examples, the sensor comprises a field-effect transistor having a source electrode, a drain electrode and a gate, and wherein the first electrode is disposed on at least one of the source electrode or the drain electrode.

An example method disclosed herein includes introducing a sample into an apparatus comprising a sensor and applying an electric potential to the sample to redistribute ions in the sample relative to the sensor. In some examples, the method includes moving the ions away from the sensor using the electric potential.

In some examples, the method includes detecting a presence of an analyte in the sample. In some such examples, detecting the presence of the analyte comprises measuring a change in at least one of a resistance, a current, a capacitance, an impedance or a voltage across the sensor. In some examples, the method includes discontinuing the electric potential prior to detecting the presence of the analyte in the sample.

FIG. 1 illustrates an example detection device or sensor 100 for measuring a concentration of a target molecule in a sample. In this example, the sensor 100 is a field effect transistor (FET) with a functionalized gate (e.g., semiconducting material). However, in other examples, the sensor 100 may be, for example, a metal-oxide-semiconductor field effect transistor (MOSFET) or any other suitable sensor or biosensor for detecting and measuring the concentration of a target molecule. As shown in the illustrated example of FIG. 1, the sensor 100 is disposed on a substrate 102 and includes a source electrode 104, a drain electrode 106 and a gate 108. The substrate 102 may comprise, for example, one or more of silicon oxide, titanium oxide, acryl resin, epoxy resin or polyimide. The gate 108 is functionalized (e.g., coated and/or doped) with a binding agent 110, which is adapted to react with a target molecule (e.g., an analyte of interest). In operation, a sample is placed in contact with the sensor. For example, as described below, a drop of the sample may be placed on the sensor, the sensor may be disposed in a flow channel containing the sample and/or the sensor may otherwise be in fluid communication with a sample. As the target molecule in the sample interacts (e.g., binds, connects, reacts) with the binding agent 110, the charge density on the gate 108 is altered. As a result, one or more of a current, a voltage and/or a resistance across the gate 108 between the source electrode 104 and the drain electrode 106 may be measured. This change in electrical property across the gate 108 is correlated with the presence and/or concentration of the target molecule in the sample. In the example shown, the binding agent 110 has been enlarged to illustrate the concept of the gate 110. However, in practical applications, the binding agent 110 may be on the order of a few atoms or molecules and, thus, the ratio of the size of the binding agent 110 to other elements of the sensor 110 may differ.

As shown in FIG. 1, ions 112 (represented by "+" and "−") (e.g., salt ions) in the sample congregate near the surface (e.g., the gate 108) of the sensor 100. The ionic charges associated with the ions 112 decrease the sensitivity of the sensor 100 by interfering with the ability of the sensor 100 to detect the change in charge density caused by the binding of the target molecule and the binding agent 110. Separating the ions 112 from the surface of the sensor 100 a distance as little as on the order of nanometers may greatly increase the sensitivity of the sensor 100, thereby allowing the sensor 100 to obtain a more accurate reading of the target molecule. As mentioned above, a Debye length is defined as the distance from a sensor surface at which ions in a solution screen (e.g., negate, interfere with) an electrical response induced by a target molecule. Example distances D1-D4 represent different Debye lengths associate various ion concentrations. The Debye length $\lambda_d$ is given by:

$$\lambda_D = \sqrt{\frac{\varepsilon_r \varepsilon_0 k_B T}{2 N_A e^2 I}} \quad \text{Equation (1)}$$

In Equation (1), $\varepsilon_r$ represents the dielectric constant, $\varepsilon_0$ represents the permittivity of free space, $k_B$ represents the Boltzmann constant, T represents the temperature in Kelvin (K), $N_A$ represents Avogadro's constant, e represents the elementary charge and I represent ionic strength of the electrolyte. For example, in FIG. 1, Debye length D1 may be 0.5 nanometers (nm), which occurs with very high ionic concentrations such as 100 millimolar (mM) solutions. In other words, in a sample having a relatively high ionic concentration such as 100 mM, the Debye length is 0.5 nm, which is the distance at which the ions in the sample screen the electrical responses generated by a target molecule on the gate 108. In some examples, when the target molecule is about 5 nm, detection of the target molecule becomes extremely difficult. In some examples, D2 represents a Debye length of 1.5 nm occurring at an ionic concentration of 10 mM, D3 represents a Debye length of 4.6 nm occurring at an ionic concentration of 1 mM and D4 represent a Debye length of 14.5 nm occurring at an ionic concentration of 0.1 mM. As the ionic concentration increases, the Debye length decreases. Thus, in some examples, to increase the ability to effectively detect target molecules, the ionic concentration of the sample at or near the sensor is decreased, thereby increasing the Debye length.

Figure 2:
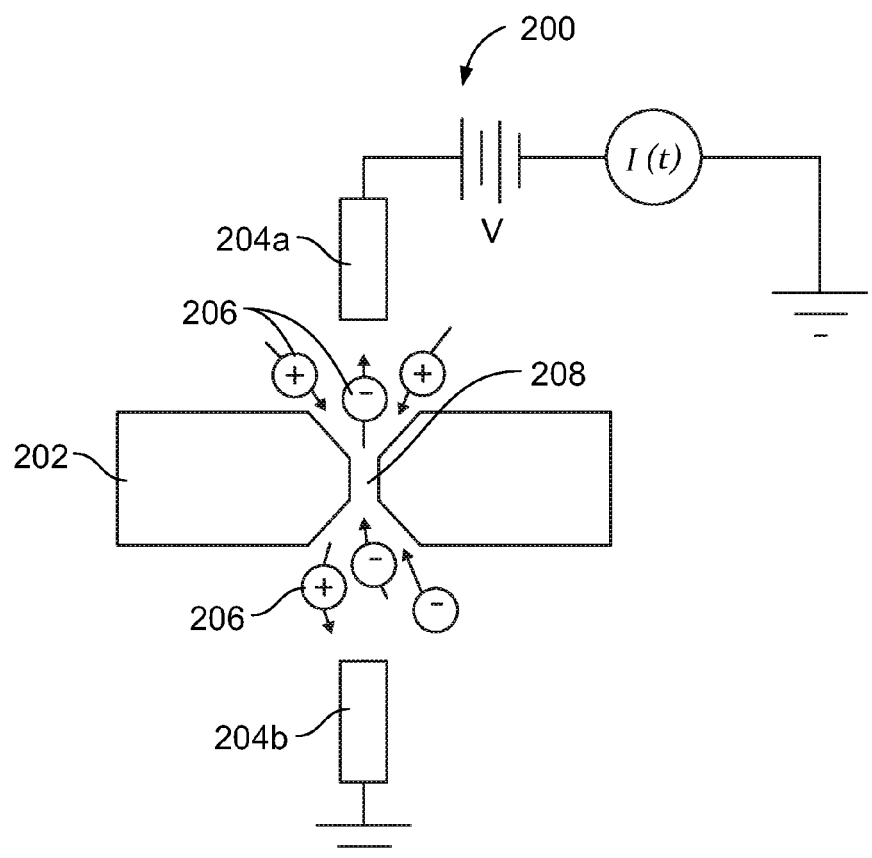
FIG. 2 illustrates an example electrode arrangement for moving ions.

FIG. 2 illustrates an example electrode device 200 used to move ions. In the example device 200 may be used to deionize or desalt a sample to move ions away from a sensor surface. As disclosed herein, the device 200 of FIG. 2 may be used to manipulate the position of ions including, for example, moving ions through a membrane 202. As shown, a first electrode 204a and a second electrode 204b create an electric potential that drives ions 206 through a nanopore 208 in the membrane 202 toward the respective counter-electrode 204a, 204b. In the example shown, the first electrode 204a provides a positive charge (e.g., voltage) and the second electrode 204b provides a negative charge and, thus, the positively charged (+) ions 206 are attracted to the second electrode 204b and the negatively charged (−) ions 206 are attracted to the first electrode 204a. In the example shown, the first and second electrodes 204a, 204b are made of silver and silver chloride. However, in other examples, other suitable material(s) may be used such as, for example, titanium, platinum, gold and/or any other suitable material.

The example apparatus, systems and methods disclosed herein provide a fast, passive methodology of mitigating the desensitizing effects of salt ions in solution. The example apparatus, systems and methods disclosed utilize one or more localized electrodes (e.g., with DC potential) to attract salt ions away from the surface of a sensor for at least a period of time sufficient to ensure an accurate reading from the sensor.

Figure 3:
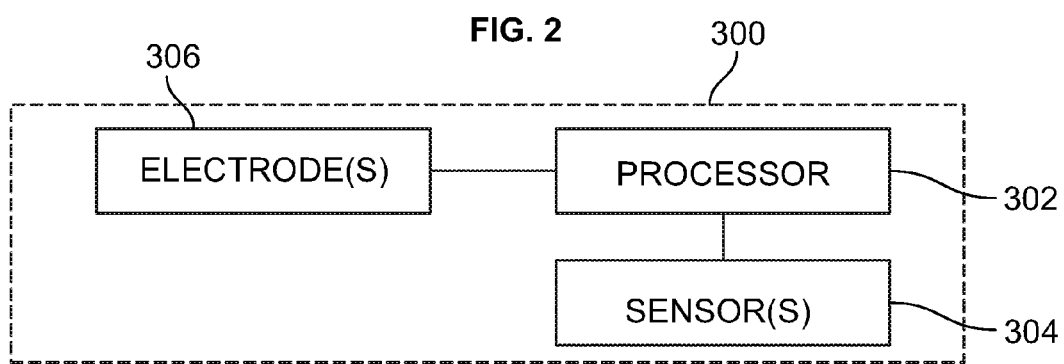
FIG. 3 is a block diagram of an example system for desalting samples in accordance with the teachings of this disclosure.

FIG. 3 is a block diagram of an example desalting system 300. The example desalting system 300 includes a processor 302 communicatively coupled to one or more sensor(s) 304 and one or more electrode(s) 306. The sensors 304 may be, for example, nanowire sensors used to measure a concentration or a presence of an analyte of interest in a sample. The electrode(s) 306 are used to create an electric potential (e.g., an electrical field, a charge) near the sensor(s) 304 to attract or migrate disruptive salt ions away from the sensor(s) 304 and towards the electrode(s) 306. In some examples, the type (e.g., DC, AC, DC+AC, etc.) and/or the strength (e.g., +1V, +2V, etc.) of the electric potential generated by the electrodes is varied. In some examples, the frequency and/or timing of an AC electric field and/or super-imposed DC field is varied.

Figure 4A:
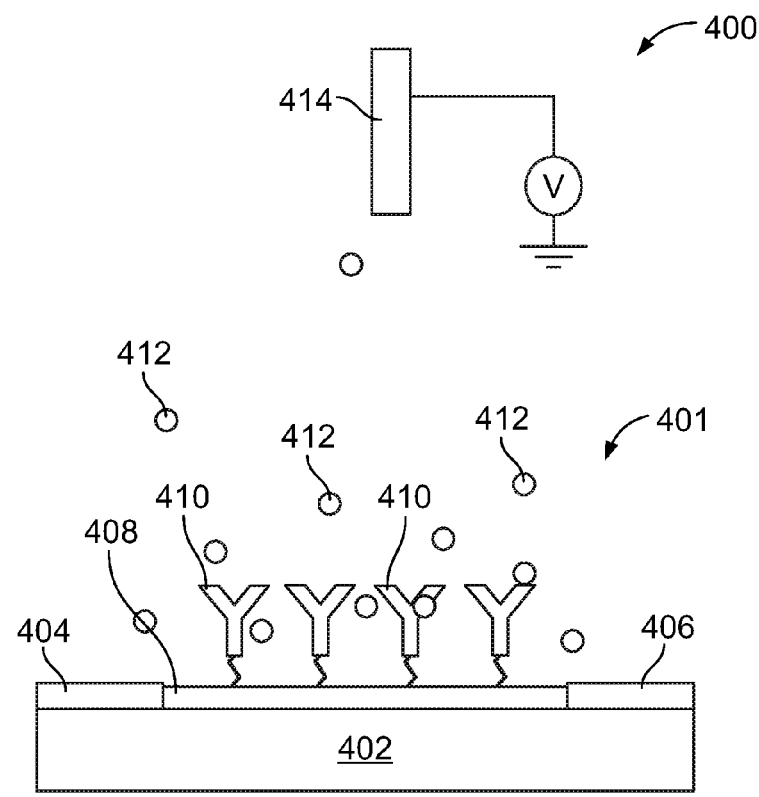
FIG. 4A shows another example system or apparatus for desalting samples having an example electrode disposed above an example sensor.
Figure 4B:
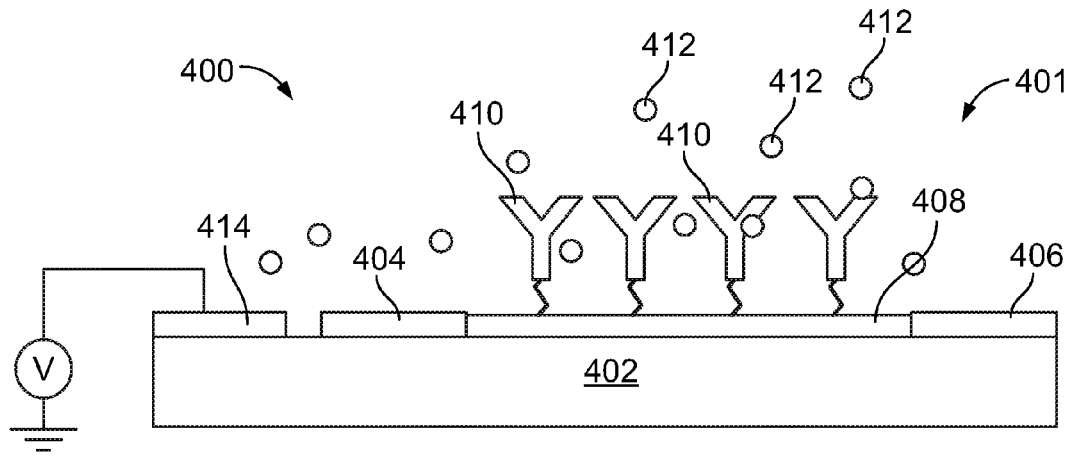
FIG. 4B shows an alternative example system or apparatus for desalting samples having an example electrode disposed on a substrate of an example sensor.

FIGS. 4A and 4B show an example system or apparatus for desalting samples 400, which may be incorporated, for example, into the system 300 of FIG. 3. As shown in FIGS. 4A and 4B, a sensor 401 is used to measure the presence and/or concentration of an analyte of interest in a sample. In the example shown, the sensor 401 is a FET and is disposed on a substrate 402. The sensor 401 includes a source electrode 404, a drain electrode 406 and a gate 408, which is functionalized with a binding agent 410. In operation, sample is placed in contact with the surface of the sensor 401, and an analyte of interest in the sample interacts with the binding agent 410 to affect the charge density at the gate 408. As shown, a plurality of ions 412 are present in the sample and congregate around the surface of the sensor 401. In examples shown in FIGS. 4A and 4B, a single electrode 414 (e.g., a desalting electrode) is provided to deionize (e.g., desalt) the sample to increase the sensitivity of the sensor 401. In the example shown in FIG. 4A, the desalting electrode 414 is disposed above or otherwise spaced apart from the sensor 401 and is to attract or repel the ions 412, depending on the charge created by the desalting electrode 414 and the charge of the ions 412.

In the example apparatus or system 400 shown in FIG. 4B, the desalting electrode 414 is disposed on the substrate 402 adjacent the sensor 401. In this example, the desalting electrode 414 is substantially coplanar with the source electrode 404, the drain electrode 406 and/or the gate 408. When the desalting electrode 414 produces an electric potential, the ions 412 are attracted and/or repelled to/by the desalting electrode 414, depending on the charge of the desalting electrode 414 and the charge of the ions 412. By moving the ions 412 away from the gate 408, the Debye length is increased and, thus, the sensitivity of the sensor 401 is also increased.

FIG. 5 shows a side view of another example system or apparatus for desalting samples 500, which may be used by, for example, the system 300 of FIG. 3. As shown in the illustrated example of FIG. 5, a sensor 501 is disposed on a substrate 502 and includes a source electrode 504, a drain electrode 506 and a gate 508, which is functionalized with a binding agent 510. In operation, a sample is placed in contact with the surface of the sensor 501, and an analyte of interest in the sample interacts with the binding agent 510 to affect the charge density at the gate 508. As shown, a plurality of ions 512 are present in the sample and congregate around the surface of the sensor 501. As mentioned above, ions tend to screen or interfere with the electrical properties generated on the gate 508. In the illustrated example, a first desalting electrode 514 and a second desalting electrode 516 are provided to move the salt ions 512 away from the surface of the sensor 501. Application of an electric potential by, for example, a direct-current (DC) moves the ions away from the sensor 501 and towards the first and second desalting electrodes 514, 516. Moving the ions away from the sensor 500 increases the Debye length (e.g., from D1 to D2) and increases the sensitivity and detection capabilities of the sensor 501. For example, prior to desalting, the sample may have a Debye length of D1, which may be smaller than the size of the binding agent 510 and/or target molecule. In such a case, the ions screen electrical charges generated on the gate 508 and interfere with the sensitivity of the sensor 501. However, when the electrical potential is applied, the negative (−) salt ions 512 are attracted to the first desalting electrode 514, and the positive (+) salt ions are attracted to the second desalting electrode 516 (or vice versa depending on the charges at the respective desalting electrodes 514, 516). As shown, the Debye length is increased to about D2 (e.g., about 20 nm), and the sensitivity of the sensor 501 is increased. In the example shown, the first and second desalting electrodes 514, 516 are silver and silver chloride electrodes. However, in other examples, other suitable material(s) may be used such as, for example, titanium, platinum, gold and/or other suitable materials.

To achieve a low ionic concentration at the surface of the sensor 501, the apparatus or system 500 includes specifically positioned electrodes 514, 516. Though two electrodes are shown in FIG. 5, any other suitable number of electrodes may also be used such as, for example, one, three, four, ten, or more electrodes. The electrodes 514, 516 may be placed in particular locations and/or geometric configurations to optimize the movement of ions away from the sensor 501. In addition, in some examples, one or more of the electrodes may be, for example, embedded on the same chip as the sensor 501 (i.e., coplanar).

In addition, in some examples, the electric potential is applied to the first and second desalting electrodes 514, 516 after the sample has been incubated. In such examples, if the analyte of interest were charged, the analyte of interest could be bound to the surface of the sensor 501 before being affected by the DC potential. Also, in some examples, the electric potential at the first and second desalting electrodes 514, 516 is turned or switched off prior to measuring the analyte of interest. In other examples, the electric potential is applied throughout the measuring the process.

Also, in the example apparatus or system 500 shown in FIG. 5, current does not flow through the sample, rather, a potential is created at the first and second desalting electrodes 514, 516. Therefore, the arrangement shown in FIG. 5 does not desalt the whole sample and/or change the chemical properties of the sample, but moves the salt ions away from the sensor 501.

The electric potential causes the salt ions in solution to electrophoretically migrate towards the first and second counter-charged desalting electrodes 514, 516. The velocity of ions in a solution may be represented by:

$$v(m/s) = \mu_{ep} E \qquad \text{Equation (2)}$$

In this equation, $\mu_{ep}$ represents the electrophoretic mobility, and E represents the strength of the electric field. The electrophoretic mobility, $\mu_{ep}$, may be determined by:

$$\mu_{ep} = q/f = \frac{q}{6\pi\eta r} \qquad \text{Equation (3)}$$

In Equation 3, q is the elementary charge of a molecule (e.g., ionic charge), f is a frictional component (e.g., collisional component), $\eta$ is the viscosity of solution, and r is the hydrodynamic radius of the ion (e.g., ionic radius).

In one example, the viscosity for a sample may be about 1.27 megapascals (MPa) (assuming Stokes approximations), the electric field is about 100 V/m (1 volt (V) separated by about 1 cm), the ionic charge of sodium is about $1.6 \times 10^{-19}$, and the hydrodynamic radius of sodium is about 0.358 nm. The resulting sodium ion velocity of this example is about 3.28 µm/s (which accounts for differences in the hydrodynamic radii of sodium ions).

In another example, the viscosity is about 1.27 MPa, and the electric field is about 500 V/m (5V separated by about 1 cm), and the ions include sodium ions having a radius of about 0.358 nm and ionic charge of 1.6×10⁻¹⁹. The resulting ion velocity of this example is about 9.35 µm/s.

In some examples, the arrangement shown in FIG. 5 reduces non-specific binding to the surface of the sensor 501. In such examples, a force felt by a charged species may be determined by:

$$F = -qE \quad \text{Equation (4)}$$

In Equation 4, q is the elementary charge of the molecule, and E is the strength of the electric field. By applying an attractive force that is greater than the binding potential, a species may be stripped off of the surface of the sensor 501. Directed application of an electric potential allows non-specifically bound species to be stripped from the sensor 501 surface while specifically bound material remain bound.

FIG. 6 is a graph of the sensitivity of the sensor 501 over time. As shown, the sensitivity increases with time because as time lapses, more ions in the solution are moved away from the sensor 501 and toward the electric potentials generated at the first and second desalting electrodes 514, 516.

FIG. 7 illustrates the example apparatus or system 500 of FIG. 5 after a period of time of operation when the salt ions 512 have been attracted to the first and second desalting electrodes 514, 516. As shown, the negative charged salt ions 512 have gathered around first desalting electrode 514 and the positively charged salt ions 512 have gathered around second electrode 516 and, thus, the negative (−) and positive (+) ions have been moved away from the surface of the sensor 501.

FIG. 8 is another graph of the sensitivity of the sensor 501 over time. As shown, the sensitivity experiences a rate of decay over time, which may happen, for example, when the desalting electric potential is lost. The rate of decay depends on variable(s) such as, for example, a diffusion rate, and/or a concentration of ions driving the diffusion rate. Diffusion may be determined by:

$$\frac{\partial \phi(r, t)}{\partial t} = \nabla \cdot [D(\phi, r) \nabla \phi(r, t)] \sim D \nabla^2 \phi(r, t) \quad \text{Equation (5)}$$

In Equation (5), D is a diffusion constant, $\phi(r, t)$ is the density of the diffusing material at location r and time t, $D(\phi, r)$ is the collective diffusion coefficient for density $\phi$ at location r, and $\nabla$ represents the vector differential operator del. The diffusion equation describes the density dynamics in a material undergoing diffusion. The rate of diffusion is proportional to the concentration of ions in the solution and, therefore, an original concentration of ions may be estimated by measuring the rate of change of concentration.

The examples disclosed herein also account for transport phenomena such as, for example, diffusion, which may occur when the electric potential is turned off prior or otherwise not continuous. For example, a sodium ion, Na+, may have a diffusion rate in serum of about 11.5 µm²/s. One second of diffusion may move the ion about 7 µm. The example apparatus and systems disclosed herein can account for diffusion when determining the duration for which to operate or apply the electrical potential to sufficiently clear the surface of the sensor from ions to achieve the desired Debye length, the desired sensitivity of the sensor and the desired concentration reading.

Figure 9:
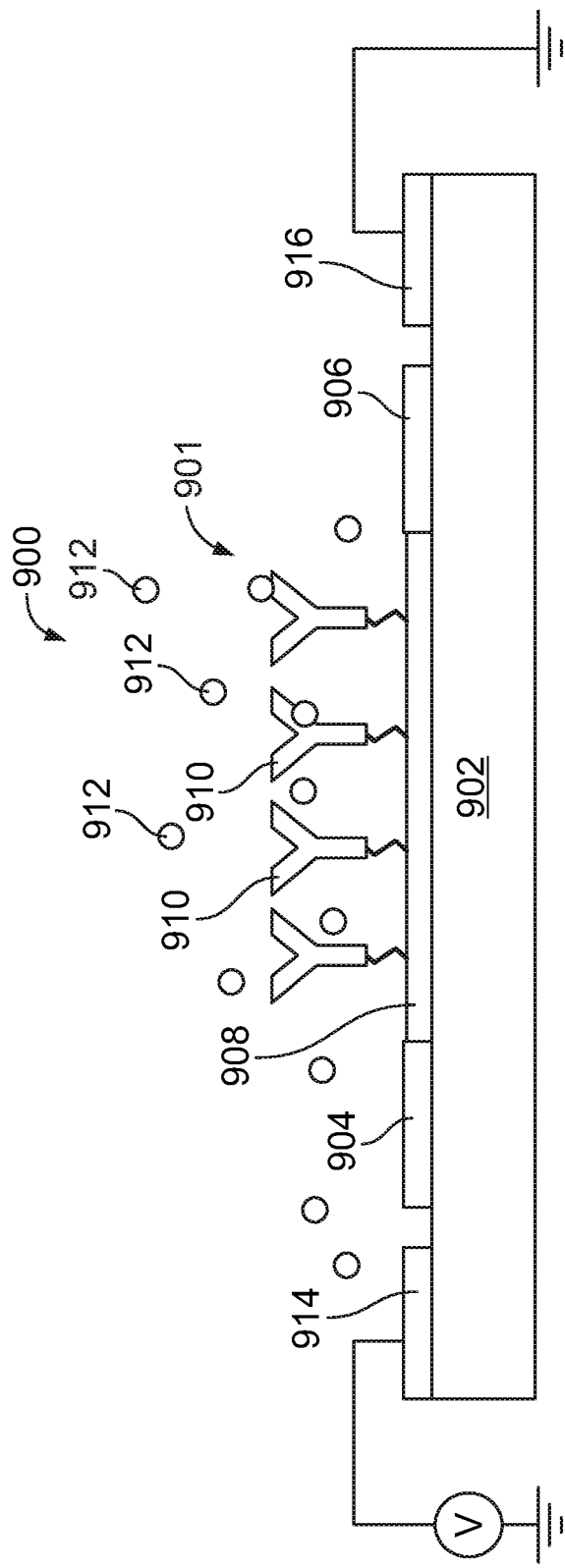
FIG. 9 shows another example system or apparatus for desalting samples having two example electrodes disposed on a substrate of an example sensor.

FIG. 9 illustrates another example system or apparatus for desalting samples 900, which may be used, for example, in the system 300 of FIG. 3. As shown a FIG. 9, a sensor 901 is an FET and is disposed on a substrate 902. The sensor 901 includes a source electrode 904, a drain electrode 906, and a gate 908, which has been functionalized with a binding agent 910. In operation, a sample is placed in contact with the surface of the sensor 901, and the analyte of interest interacts with the binding agent 910 on the gate 908. As shown, ions 912 congregate near the surface of the sensor 901 and may screen the electric response(s) generated at the gate 910. In this example, a first desalting electrode 914 and a second desalting electrode 916 are provided on the substrate 902 to move the ions 912 away from the surface of the gate 908. The first and second desalting electrodes 914, 916 are substantially coplanar with the source electrode 904, the drain electrode 906 and/or the gate 908. In the example arrangement shown in FIG. 9, the first desalting electrode 914 is spaced from the source electrode 904 and the second desalting electrode 916 is spaced from the drain electrode 906. In this example, the first desalting electrode 914, the source electrode 904, the drain electrode 906 and the second desalting electrode 916 are in a linear arrangement with the gate 908. The electric potential created by the first and second desalting electrodes 914, 916 attracts the ions 912, moves the ions 912 in the sample away from the gate 908 and, thus, reduces the screening caused at the gate 908.

Figure 10:
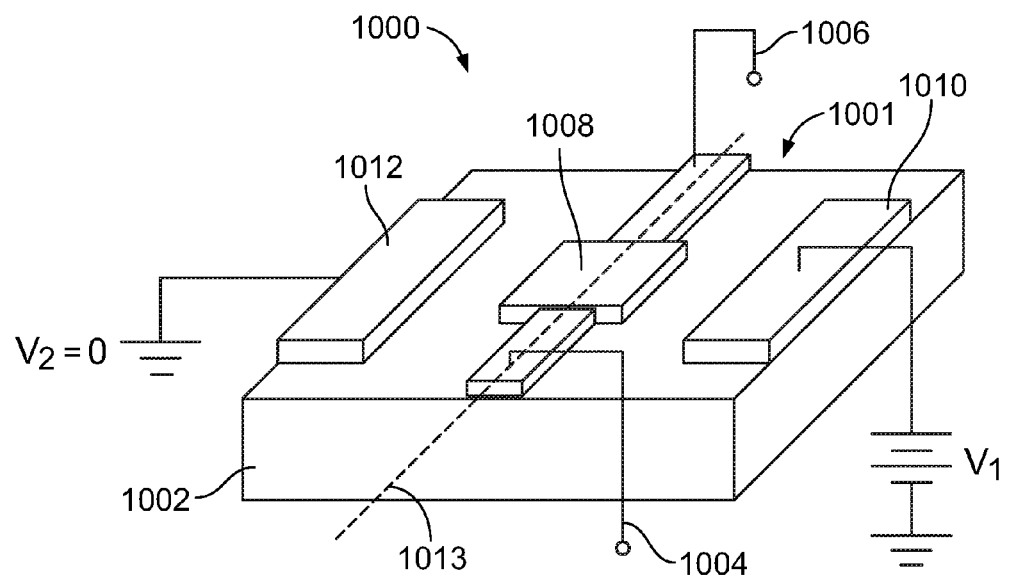
FIG. 10 is a perspective view of an example system or apparatus for desalting samples having two example electrodes disposed on a substrate of an example sensor where one electrode applies a potential.
Figure 11:
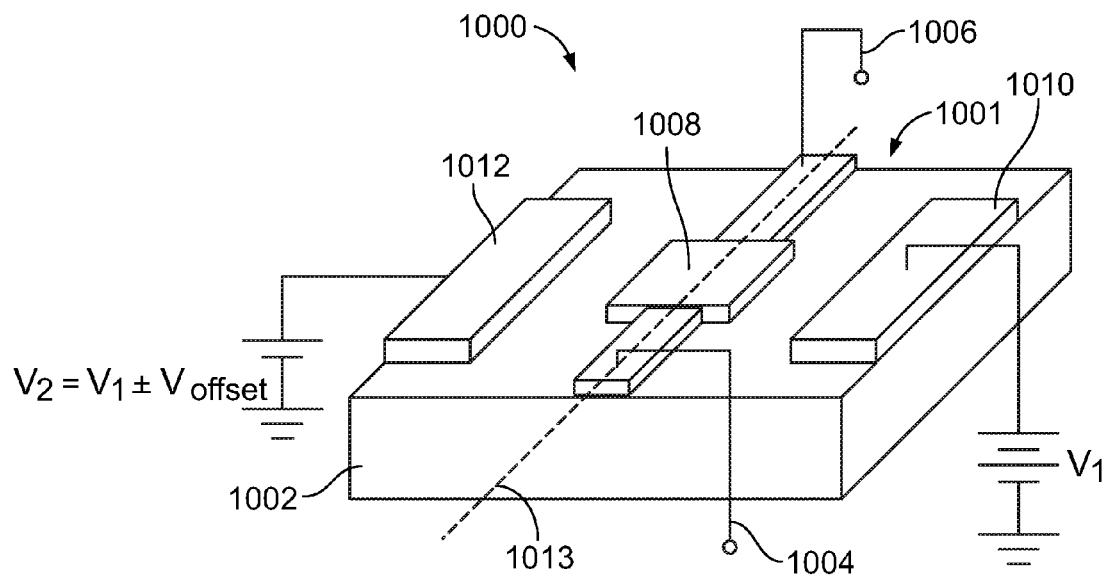
FIG. 11 is a perspective view of the example system or apparatus of FIG. 10 where both electrodes apply a potential.

FIGS. 10 and 11 show another example system or apparatus for desalting samples 1000, which may be incorporated, for example, into the system 300 of FIG. 3. In the example shown, a sensor 1001 is disposed on a substrate 1002 and includes a source electrode 1004, a drain electrode 1006 and a gate 1008, which is functionalized with a binding agent. A first desalting electrode 1010 and a second desalting electrode 1012 are disposed on the substrate 1002 and are provided to move ions in a sample away from the surface of the gate 1008. In the example shown, the first and second desalting electrodes 1010, 1012 are substantially coplanar with the source electrode 1004, the drain electrode 1006 and/or the gate 1008. In the arrangement shown, the source electrode 1004, the gate 1008 and the drain electrode 1006 are linearly aligned along an axis 1013. In addition, the first desalting electrode 1010 is disposed on a first side of the axis 1013, and the second desalting electrode 1012 is disposed on a second side of the axis 1013, opposite the first side. Also in this example, the first and second desalting electrodes 1010, 1012 are spaced apart from the axis 1013. The relative lengths of the first and second desalting electrodes 1010, 1012 and/or the respective distances of the first and second desalting electrodes 1010, 1012 from the gate 1008 affect the sensing behavior of the sensor 1001. In some examples, smaller desalting electrodes placed further from the axis 1013 will increase the sensitivity of the sensor 1001 less than larger desalting electrodes placed closer to the axis 1013. In some examples, positioning the desalting electrodes 1010, 1012 too close to the sensor 1001 may create an electric field that may cause dielectric breakdown of various materials in the sample. Therefore, the dimensions and parameters disclosed above may be adjusted to optimize the sensing behavior of the sensor 1001.

In the illustrated examples of FIGS. 10 and 11, the first desalting electrode 1010 has an electric potential represented by $V_1$, and the second desalting electrode 1012 has an electric potential represented by $V_2$. The electric potential $V_1$ may be a positive or a negative voltage applied to the first desalting electrode 1010 (e.g., +1V, −1V, +0.25 mV, −0.25 mV, etc.). In the illustrated example shown in FIG. 10, the second desalting electrode 1012 is grounded, and the electric potential $V_2$ of the second desalting electrode 1012 is substantially zero (0). In this example, if $V_1$ is a positive voltage, negative ions in the sample are attracted to the first desalting electrode 1010. Conversely, if $V_1$ is a negative voltage, positively charged ions in the sample are attracted to the first desalting electrode 1010.

In the illustrated example shown in FIG. 11, the electric charge $V_2$ is $V_1$ plus or minus (±) an offset voltage ($V_{offset}$) and, thus, the second desalting electrode 1012 also has a positive or negative potential (e.g., +1V, −1V, +0.25 mV, −0.25 mV). Therefore, in some examples, the first desalting electrode 1010 produces a positive potential and the second desalting electrode 1012 produces a negative potential (e.g., $V_1$=+1V and $V_2$=−1V). In other examples, both the first desalting electrode 1010 and the second desalting electrode 1012 produce a positive or negative potential (e.g., $V_1$=+0.5V and $V_2$=+1.5V). Thus, in some examples, only one desalting electrode has a substantive potential while the other desalting electrode is a ground or neutral electrode, and in other examples, both of the desalting electrodes have substantive charges.

Figure 12:
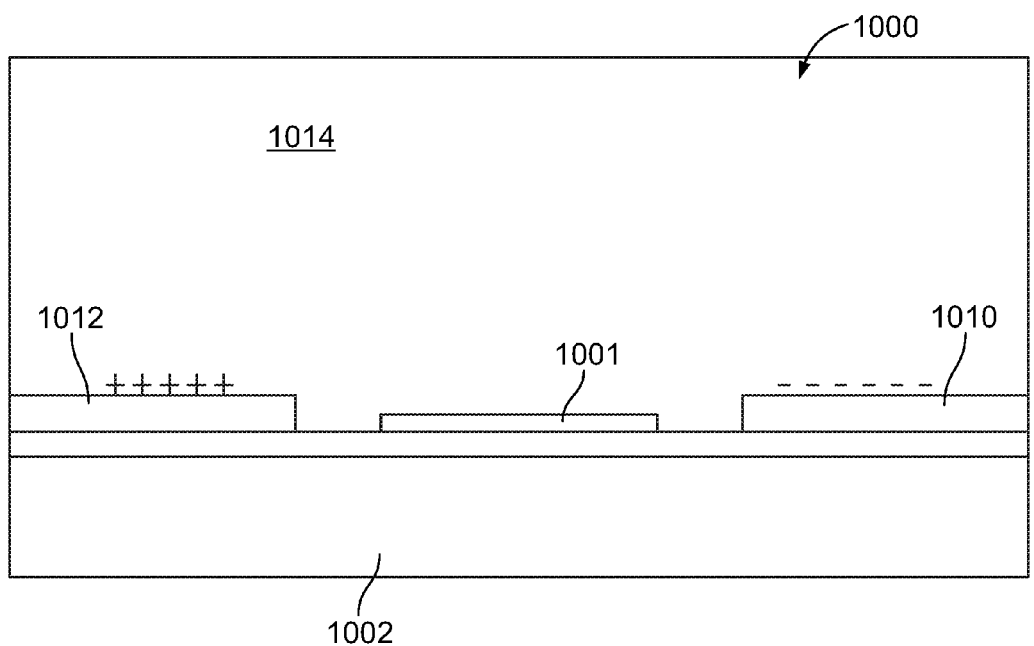
FIG. 12 illustrates an example system or apparatus for desalting samples in use in a bulk sample supply system having a flow channel.

FIG. 12 shows the example apparatus or system 1000 shown in FIGS. 10 and 11 as used in a bulk sample supply system. In the illustrated example, a flow of sample 1014 is provided past or over the sensor 1001. The flow of sample 1014 may be provided in a flow channel (e.g., a microfluidic flow channel) having a sample that is to be tested. As mentioned above, the first and second desalting electrodes 1010, 1012 are provided to move ions in the sample 1014 away from the surface of the sensor 1001. As the sample 1014 flows over the sensor 1001, the first and second desalting electrodes 1010, 1012 are activated to move the ions away from the sensor 1001. As shown, the negative ions (−) have been moved at or near the first desalting electrode 1010 and away from the surface of the sensor 1001, and the positive ions (+) have been moved at or near the second desalting electrode 1012 and away from the surface of the sensor 1001. The example sensor 1001 may be any sensor/electrode arrangement disclosed herein. Thus, any sensor/electrode arrangement described herein may be incorporated into a sample flow channel for testing a sample while the sample is flowing through the flow channel and in contact with the sensor and electrode arrangement. In other examples, the sample is stationary on the sensor and electrode such as, for example, in a well.

Figure 13A:
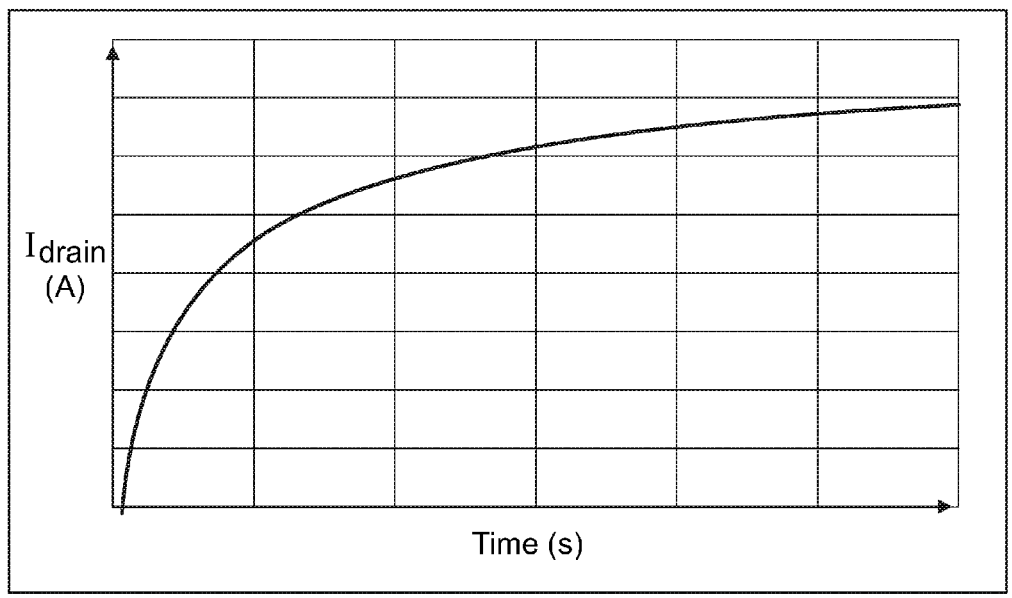
FIG. 13A is a graph of an example plot of current at a drain electrode versus time.

FIGS. 13A-E are graphs representing example relationships between different properties of the example sensor and electrode arrangements disclosed herein. Specifically, FIG. 13A shows the current at the drain electrode ($I_{drain}$) (e.g., the drain electrode 1006) over time. The desalting electrodes are activated at time zero (0), and, as time increases, the current at the drain generally increases. The current at the drain is indicative of charge density cause by target molecules in the sample. Thus, as time increases and more ions are moved away from the sensor (e.g., the sensor 1000), the amount of current detected across the gate (e.g., the gate 1008) also increases. After a period of time, the amount of current at the drain eventually levels or remains constant or near constant over time. In some examples, the leveling of the drain current occurs because a potentially maximum amount of the ions in the sample have been removed from or moved away from the sensor. In other examples, such as samples with high ionic concentrations, the desalting electrodes may attract a limited capacity of ions. Once the surfaces of the desalting electrodes are substantially covered by ions, additional ions in the sample remain dispensed in the sample.

Figure 13B:
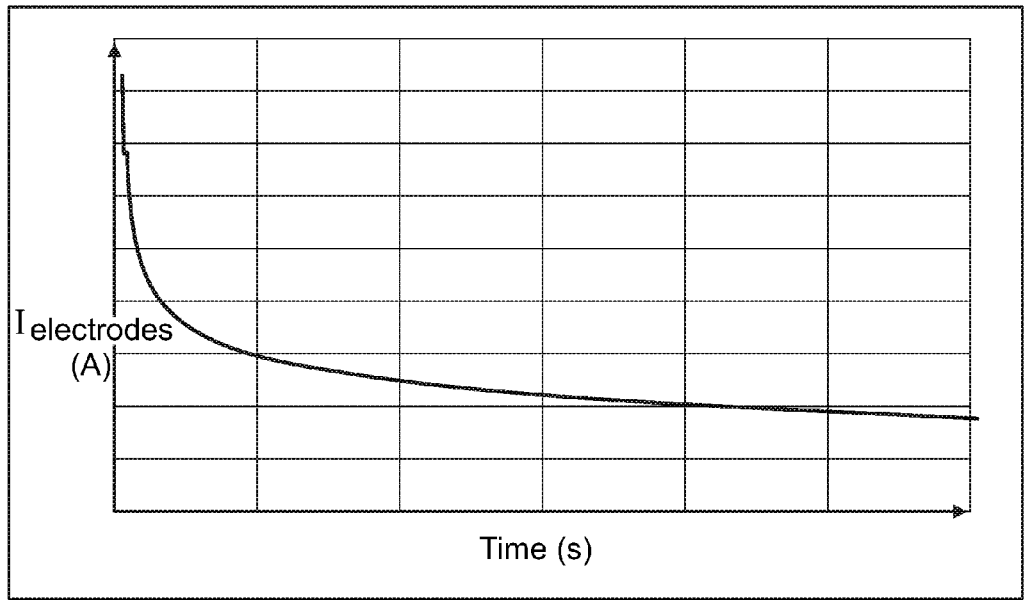
FIG. 13B is a graph of an example plot of current at an example desalting electrode versus time.

FIG. 13B is a graph showing the current generated at the desalting electrodes ($I_{electrodes}$) versus time as averaged over different electrode voltages. The desalting electrodes are activated at time zero (0). When the desalting electrodes are initially activated, there is a high current at the desalting electrodes, which is the result of the ions rapidly moving toward the desalting electrodes. As time increases, the current at the desalting electrodes decreases and generally levels (e.g., remains constant or near constant) over time. In some examples, the leveling occurs because movement of the ions has decreased and a potentially maximum amount of the ions have already been attracted to the desalting electrodes. In other examples, such as samples with high ionic concentrations, the desalting electrodes may attract a limited capacity of ions. Once the surfaces of the desalting electrodes are substantially covered by ions, additional ions in the sample remain dispensed in the sample.

Figure 13C:
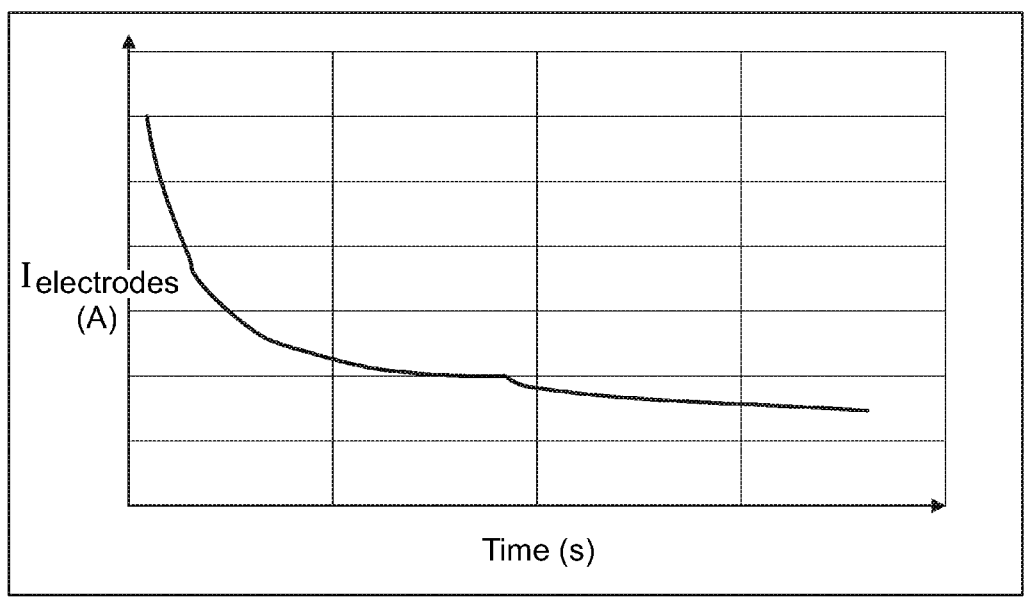
FIG. 13C is a graph of an example plot of current at a desalting electrode versus time.

FIG. 13C is a graph showing the current generated at the desalting electrodes versus time as average over different ionic concentrations of the samples. The desalting electrodes are activated at time zero (0). As shown, when the electrodes are initially activated, there is a high current at the electrodes, which is the result of the ions rapidly moving toward the electrodes. Similar to the trend shown in FIG. 13B, as time passes, the current at the electrodes decreases and generally tapers off for the reasons noted above.

Figure 13D:
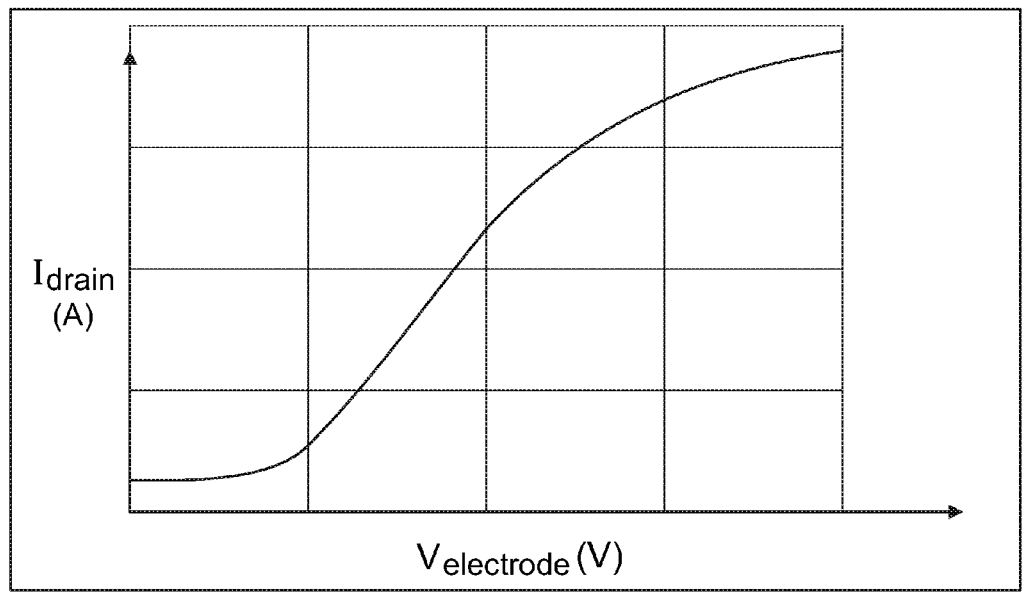
FIG. 13D is a graph of an example plot of current at a drain electrode versus voltage at an example desalting electrode.

FIG. 13D is a graph showing the current at the drain electrode ($I_{drain}$) relative to the voltage of the desalting electrode(s). As shown, as the voltage in the desalting electrodes is increased, the current at the drain (e.g., across the gate) also increases. As mentioned above, as the ions in the sample are moved away from the sensor, the change in charge density on the sensor is more easily detected and a current may flow from the source electrode to the drain electrode. Increasing the voltage of the desalting electrode(s), creates a higher electric field to more rapidly and effectively attract/repel ions in the sample.

Figure 13E:
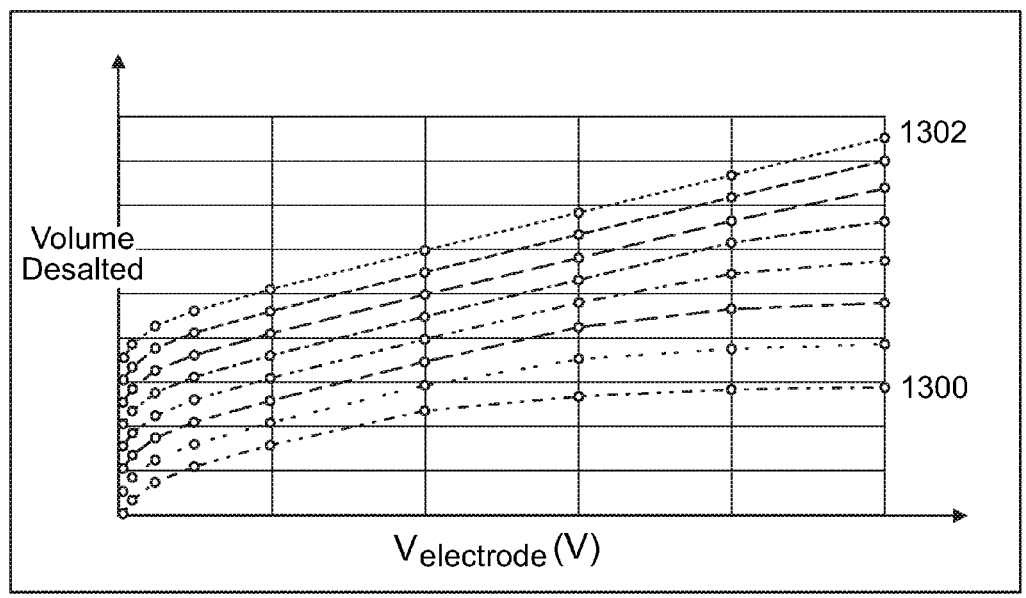
FIG. 13E is a graph of example plots of volumes of sample desalted versus voltages of an example desalting electrode.

FIG. 13E is a graph showing the amount of voltage needed to desalt different volumes of samples having different ionic concentrations to approximately 1% of their bulk concentration. The line 1300 represents a sample having a relatively high ionic concentration (e.g., 1000 mM) and line 1302 represents a sample having a relatively low ionic concentration (e.g., 0.0001 mM). The lines between line 1300 and 1302 represent sample with increasing ionic concentrations between that of 1300 and 1302. As shown, with the samples having lower ionic concentrations (e.g., line 1302), the amount of samples that could be desalted (e.g., to approximately 1% of its bulk concentration) is higher than the samples with higher ionic concentrations (e.g., line 1300). This example illustrates that samples with lower ionic concentrations can be desalted more readily and with lower electrode voltages than samples with higher ionic concentrations.

FIG. 14 shows a side view of an example system or apparatus for desalting samples 1400, which may be incorporated, for example, into the system 300 of FIG. 3. In the example shown, a sensor 1401 is disposed on a substrate 1402 between a first electrode 1404 and a second electrode 1406. The first and second electrodes 1404, 1406 provide an electric potential to move ions in a sample 1408 away from the surface of the sensor 1401. In this example, the height of the first and second electrodes 1404, 1406 relative to the height of the sensor 1401 has been increased. By increasing the height of the first and second electrodes 1404, 1406, the first and second electrodes 1404, 1406 have more surface area to attract ions in the sample 1408. Thus, more ions can be attracted by the first and second electrodes 1404, 1406.

In some examples, the length of the first and second electrodes 1404, 1406 may also be changed. FIG. 15A is an example top view of the apparatus or system shown in FIG. 14. In the example shown in FIG. 15A, a well 1500 defined by the sensor 1401 and the first and second electrodes 1404, 1406 is substantially square shaped. As shown, the width W1 of the first and second electrodes 1404, 1406 is relatively narrower compared to the width W2 of the substrate 1402. FIG. 15B shows an alternative top view of apparatus or system of FIG. 14, where the width W3 of the first and second electrodes 1404, 1406 is wider relative to W2 than the example shown in FIG. 15A. As shown in the example in FIG. 15B, a well 1502 defined by the sensor 1401 and the first and second electrodes 1404, 1406 is substantially rectangular. In both of the examples, as shown in FIGS. 15A and 15B, sample may travel between the first and second electrodes 1404, 1406 and over the surface of the sensor 1401. By changing the height and the width of the electrodes, the relative surface area of the first and second electrodes 1404, 1406 is changed and, thus, may affect the sensing behavior of the sensor 1401. For example, wider and/or higher or deeper desalting electrodes may move a greater number of ions and increase the sensitivity of the sensor 1401.

Figure 16A:
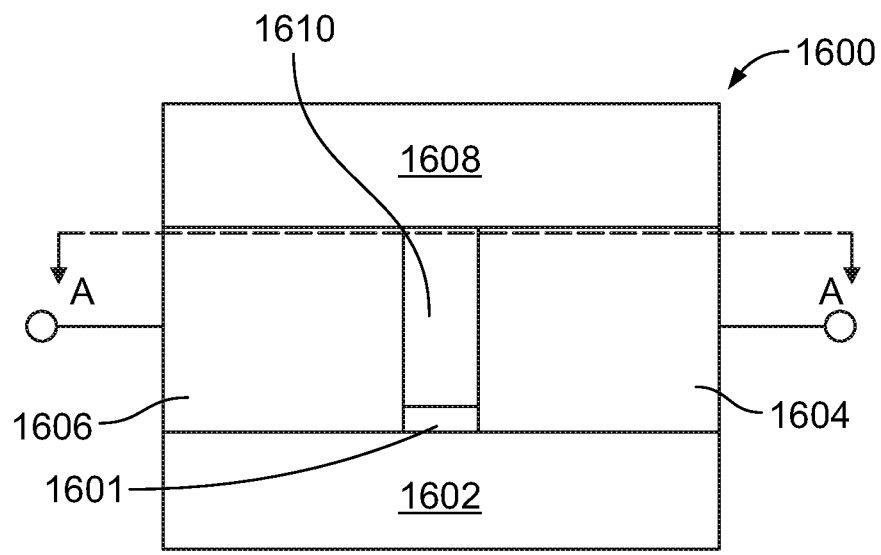
FIG. 16A is a side view of an example system or apparatus for desalting samples with an example a flow channel.

FIG. 16A is a side view of another example system or apparatus for desalting samples 1600 that may be incorporated, for example, into the system 300 of FIG. 3. In the example shown, a sensor 1601 is disposed on a first substrate 1602 between a first electrode 1604 and a second electrode 1606. A second substrate 1608 is disposed on top of the first and second electrodes 1604, 1606 and, thus, a flow channel 1610 is formed by the second substrate 1608, the first and second electrodes 1604, 1606, the sensor 1601 and the first substrate 1602. The first and second electrodes 1604, 1606 provide an electric potential to move ions in a sample, flowing through the channel 1610, away from the surface of the sensor 1601. In this example, similar to the example shown in FIG. 14, the height of the first and second electrodes 1604, 1606 relative to the height of the sensor 1601 has been increased than shown in some prior examples. By increasing the height of the first and second electrodes 1604, 1606, the first and second electrodes 1604, 1606 have more surface area to attract ions in the sample.

Figure 16B:
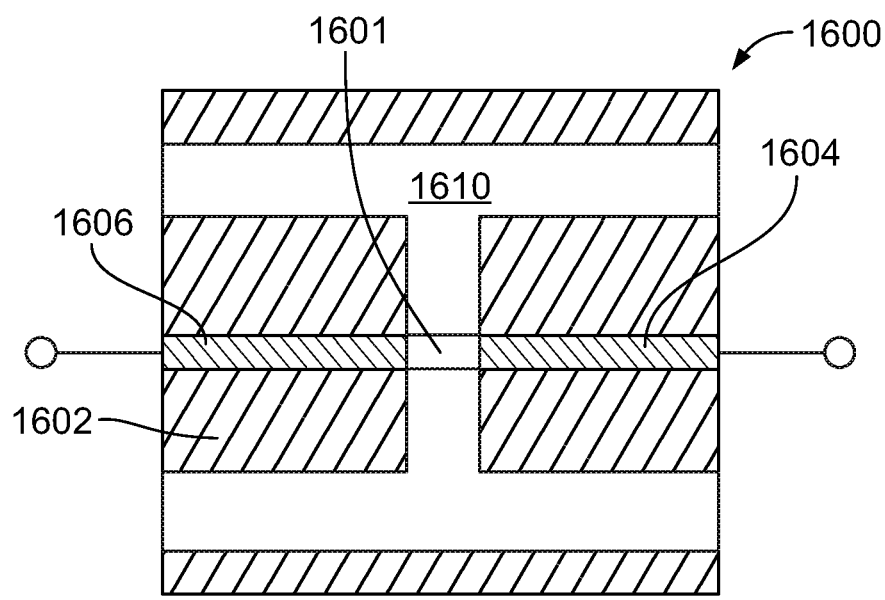
FIG. 16B is a cross-sectional view of the example system or apparatus of FIG. 16A taken along the A-A line.

FIG. 16B is a cross-sectional view of the sensor and electrode arrangement shown in FIG. 16A taken along the A-A line. As shown, the flow channel 1610 includes branches, and the sample fluid may enter through one or more of the sides and across the surface of the sensor 1601 between the first and second electrodes 1604, 1606.

Figure 17:
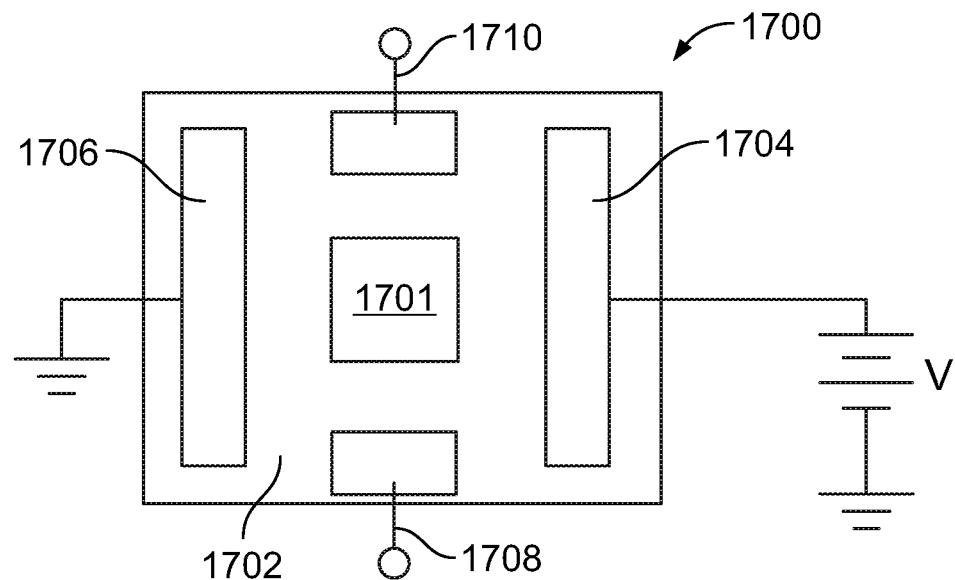
FIG. 17 is a schematic of an example system or apparatus for desalting samples having multiple example electrodes disposed around an example sensor.

FIG. 17 illustrates another system or apparatus for desalting samples 1700, which may be incorporated, for example, into the system 300 of FIG. 3. In the example shown, a sensor 1701 is disposed on a substrate 1702 between a first electrode 1704, a second electrode 1706, a third electrode 1708 and a fourth electrode 1710. In some examples, the first, second, third and fourth electrodes 1704-1710 are all desalting electrodes and provide electrical potential(s) to move ions away from the sensor 1701. In some examples, the electrodes 1704-1710 may be paired together, such that one electrode provides a positive electric potential and the other electrode provides a negative electric potential. For example, the first electrode 1704 and the third electrode 1708 may provide a positive electrical potential and the second electrode 1706 and the fourth electrode 1710 may provide a negative electrical potential. In such an example, negative ions in the sample would migrate toward the positive electric potential created by the first electrode 1704 and the third electrode 1708. Likewise, positively charged ions in the sample would migrate toward the negative electric potential created by the second electrode 1706 and the fourth electrode 1710. In other examples, one of the pair of electrodes may provide a substantive potential (e.g., a positive or negative potential) and the other electrode may be a ground (e.g., provide substantially zero (0) potential).

In the example system or apparatus 1700 shown, the first, second, third and fourth electrodes 1704-1710 are substantially coplanar with the sensor 1701 and arranged in a square pattern around the sensor 1701. The distance between each of the electrodes 1704-1710 and the sensor 1701 may be altered to change the sensing behavior of the sensor 1701, as disclosed herein. Also, in this example, the first and second electrodes 1704, 1704 are relatively longer than the third and fourth electrodes 1708, 1710. In other examples, more or fewer electrodes are provided on the substrate 1702 and may be configured in other arrangements. Also, in some examples, each electrode may have a unique dimension, all may have identical dimensions, and/or any combination of repeating and/or unique shape(s) and/or size(s).

In some examples, the first and second electrodes 1704, 1706 are desalting electrodes and the third and fourth electrodes 1708, 1710 are sensing electrodes for an additional device such as, for example, an impedance sensor. In such an example, the third and fourth electrodes 1708, 1710 are used to measure the electrical resistance in the sample, which may be used to verify the desalting operation.

Figure 18:
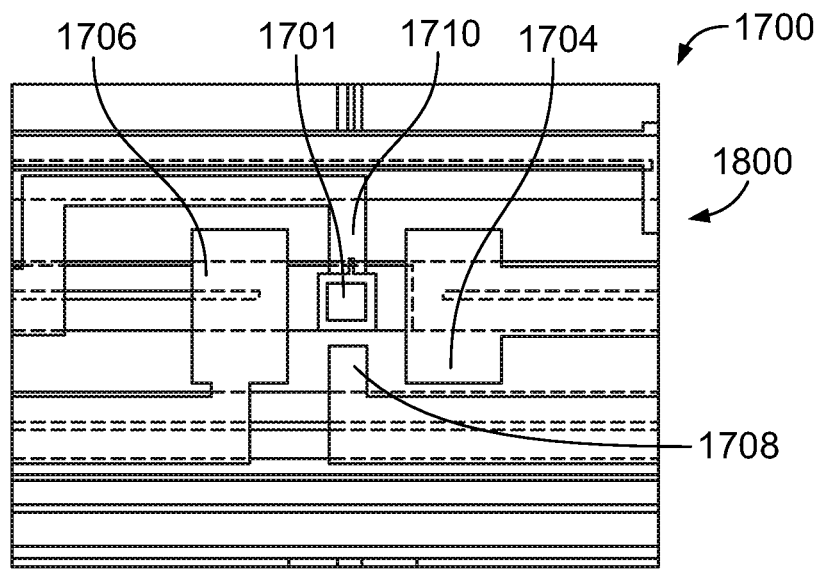
FIG. 18 shows an example microchip implementing the system or apparatus of FIG. 17.

FIG. 18 shows a portion of microchip sensor 1800 having the example system or apparatus 1700 shown in FIG. 17, and which may be incorporated, for example, into the system 300 of FIG. 3. As shown, the sensor 1701 and the electrodes 1704-1710 are disposed on the surface of the microchip 1800. A sample may be applied to the microchip 1800 and the sensor 1701 detects the concentration of a target molecule in the sample. Similar to the example described in FIG. 17, one or more of the electrodes 1704-1710 function as desalting electrodes to move ions away from the sensor 1701. In some examples, the electrodes 1704-1710 operate in pairs.

Figure 19:
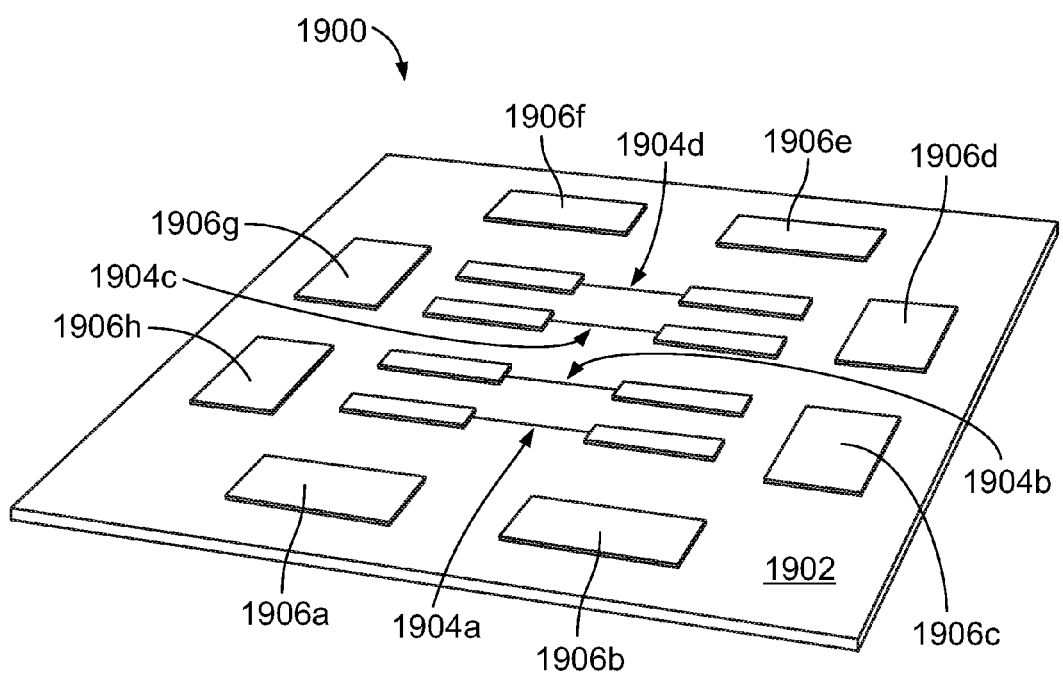
FIG. 19 is a perspective view of another example system or apparatus for desalting samples with multiple electrodes and multiple sensors.

FIG. 19 is an example system or apparatus for desalting samples 1900. The example arrangement 1900 may be incorporated, for example, into the system 300 of FIG. 3. The example system or apparatus 1900 includes a chip 1902 on which sensors 1904a, 1904b, 1904c, 1904d (e.g., biosensor, nanowire sensors, FETs) and a plurality of electrodes 1906a, 1906b, 1906c, 1906d, 1906e, 1906f, 1906g, 1906h are disposed. In other examples, the system or apparatus 1900 may include more or fewer electrodes. The example sensors 1904a-d detect biomolecules or biomolecular binding events. In addition, the example electrodes 1906a-h may be insulated such that a current does not flow through the solution.

In the example shown, the sensors 1904a-d are substantially surrounded by the electrodes 1906a-h on the chip 1902. The electrodes 1906a-h are positioned away from and apart from the sensors 804a-d and create an electrical potential such that counter-charged ionic salt species in a sample migrate towards the electrodes 1906a-h and away from the sensors 1904a-d. The migration of the salt ions increases both the Debye length and the sensitivity of the sensors 1904a-d. The example system or apparatus 1900 shown allows the sample to be desalted (i.e., deionized) on the chip rather than an external process being needed.

As shown in the example system or apparatus 1900 (and other examples disclosed herein), the electrodes 1906a-h (and the electrodes of other examples disclosed herein) also remove non-specifically bound proteins from the sensor surface. Many proteins in solutions maintain a net ionic charge and, therefore, the proteins may be attracted towards the electrodes 1906a-h. Because the specifically bound proteins are more strongly bound, the potential necessary to detach the proteins is higher than the potential necessary to detach non-specifically bound proteins. Thus, it is possible to minimize non-specific binding on a sensor surface. Other ions such as, for example, sodium, potassium, and chloride ions may also be directed towards the electrodes on the sensor surface, thereby locally desalting the sample and allowing for a low ionic content during sensor measurements.

In the example of FIG. 19, there are eight electrodes 1906a-h forming a square-shaped perimeter around the plurality of sensors 1904a-d. In particular, there are two electrodes per side of the square. In other examples, there are multiple other arrangements. For example, the number of electrodes may be varied. The shape and/or the geometry of one or more of the electrode(s) may be varied. Some examples may include electrodes in a ring shape, electrodes in an elliptical shape, two parallel lines of electrodes, intersecting lines of electrodes, an arc of electrodes, a single side of electrodes, and/or any other suitable pattern. Also, in some examples, one or more of the electrode(s) may be coplanar with the sensors and in other examples, the one or more of the electrode(s) may not be co-planar with one or more of the sensor(s).

Figure 20A:
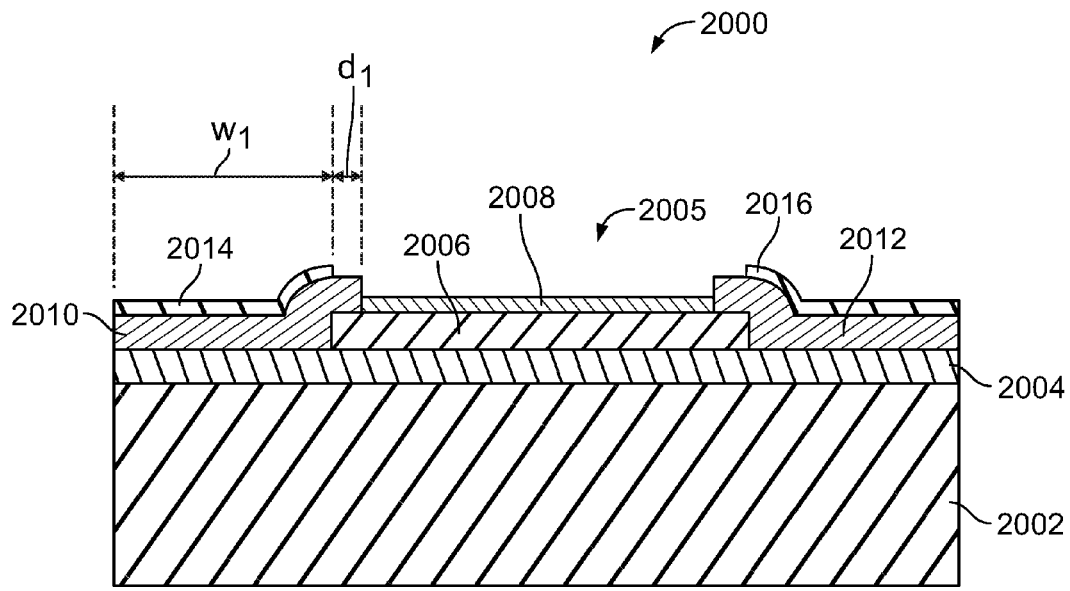
FIG. 20A is a side view of an example system or apparatus for desalting samples.
Figure 20B:
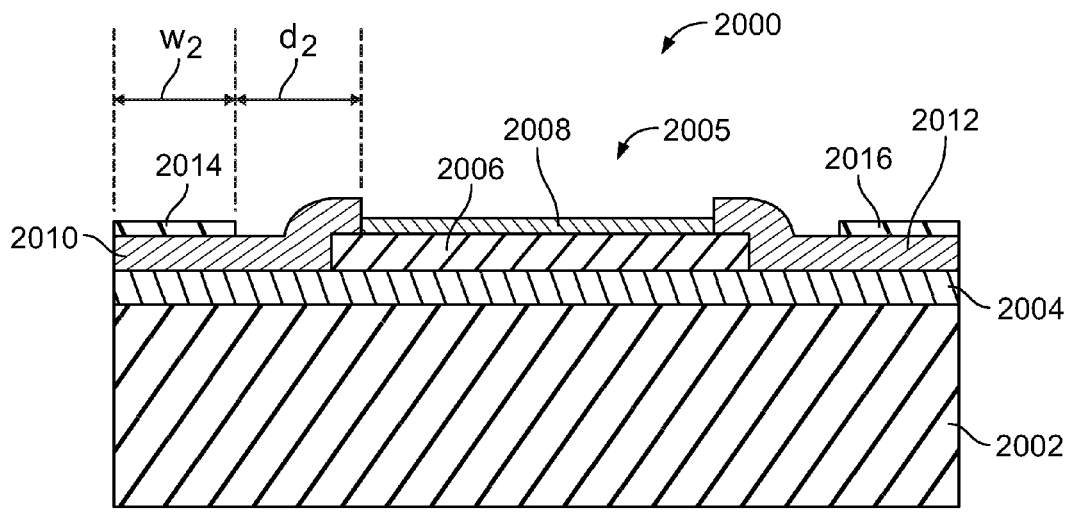
FIG. 20B is a side view of an alternative example system or apparatus for desalting samples.

FIGS. 20A and 20B show cross-sectional views of an example system or apparatus for desalting samples 2000 disposed on a substrate 2002, which may include, for example, a silicon chip, a microchip, etc. In the example of FIGS. 20A and 20B, an insulator layer 2004 (e.g., a layer of buried oxide, silicon dioxide) is disposed on the substrate 2002. A sensor 2005 such as, for example, an FET sensor, is disposed on the substrate 2002 and includes a gate 2006 (e.g., a TiN extended gate) that, in this example, includes an insulator layer 2008 (e.g., hafnium oxide ($HfO_2$)). The gate 2006 is disposed between a first inter-layer dielectric insulator 2010 and a second inter-layer dielectric insulator 2012. In the example shown, a first electrode 2014 (e.g., a desalting electrode) is layered on the first inter-layer dielectric insulator 2010 and a second electrode 2016 (e.g., a desalting electrode) is layered on the second inter-layer dielectric insulator 2012. The first and second electrodes 2014, 2016 may comprise any suitable electrode material(s) such as, for example, gold, platinum, silver, silver chloride, titanium and/or other suitable material(s).

In the example shown in FIG. 20A, the first and second electrodes 2014, 2016 are layered onto the first and second inter-layer dielectric insulators 2010, 2012, respectively, and are separated a distance $d_1$ from the edge of the respective first and second inter-layer dielectric insulators 2010, 2012 and, thus, the edge of the gate 2006 of the sensor 2005. Additionally, in the example shown in FIG. 20A, the first and second electrodes 2014, 2016 have a width or length of $w_1$. The distances $d_1$ and $w_1$ may be varied to affect the sensing behavior of the sensor 2000. For example, as shown in FIG. 20B, the distance $d_2$ is greater than $d_1$ and the distance $w_2$ is smaller than the distance $w_1$ in FIG. 20A.

FIGS. 21A-D show cross-sectional views of an example system or apparatus for desalting samples 2100, which may be, for example, an on-chip electrode sensor and electrode device. FIGS. 21A-D illustrate an example fabrication process of the example system or apparatus 2100. The example sensor 2100 includes a substrate 2101 which may be, for example, an FET sensing chip. The sensor 2100 also includes an insulator layer 2102, which may include, for example, a buried oxide. In addition, the example sensor 2100 includes a first electrode layer 2104, which may include, for example, gold. A sensor 2105 having a gate 2106 (e.g., a TiN extended gate) that is disposed on the first insulator layer 2102 is also included. The gate 2106 is disposed between a first inter-layer dielectric insulator 2108 and a second inter-layer dielectric insulator 2110. In addition, an insulator layer 2112 is disposed over the gate 2106. The insulator layer 2112 may be, for example, $HfO_2$.

Figure 21A:
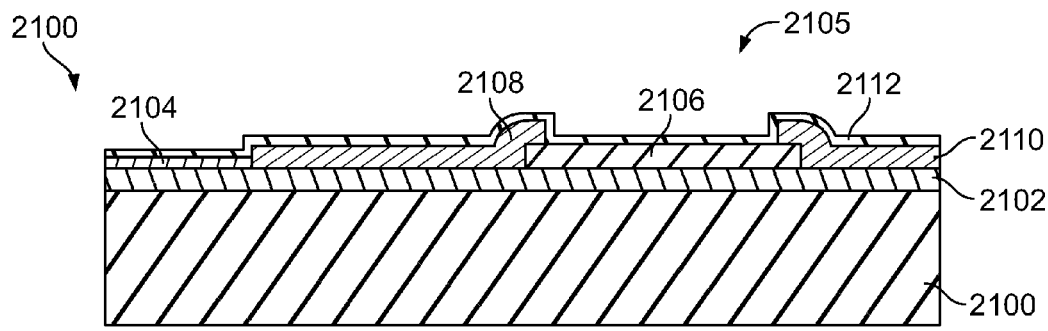
FIGS. 21A-D illustrate an example fabrication process for creating an example system or apparatus for desalting samples on a chip.
Figure 21B:
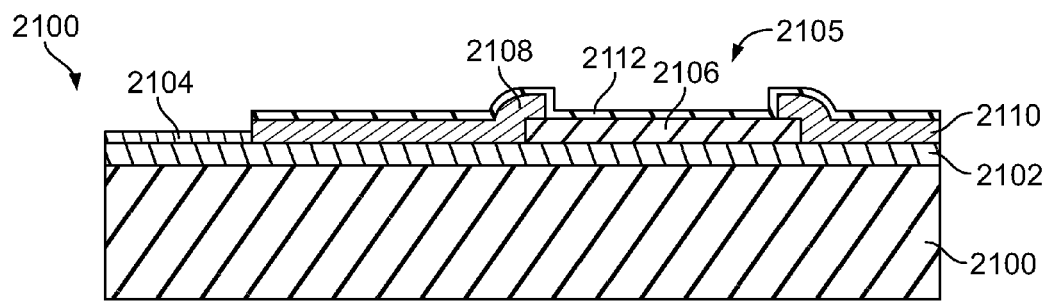

A portion of the insulator layer 2112 is removed by, for example, wet etching to expose the electrode layer 2104 as shown in FIG. 21B. Removal of a portion the insulator layer 2112 to expose at least a portion of the electrode layer 2104 assists in low temperature wire-bonding for coupling the desalting electrodes at the macroscopic level to, for example, a printed circuit board (PCB) and/or card reader.

Figure 21C:
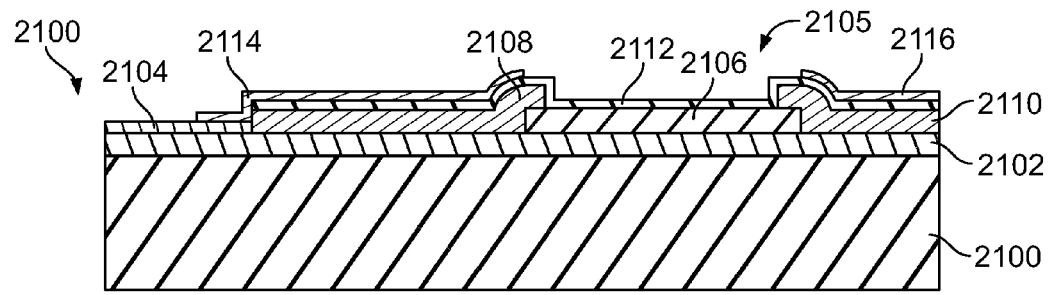
Figure 21D:
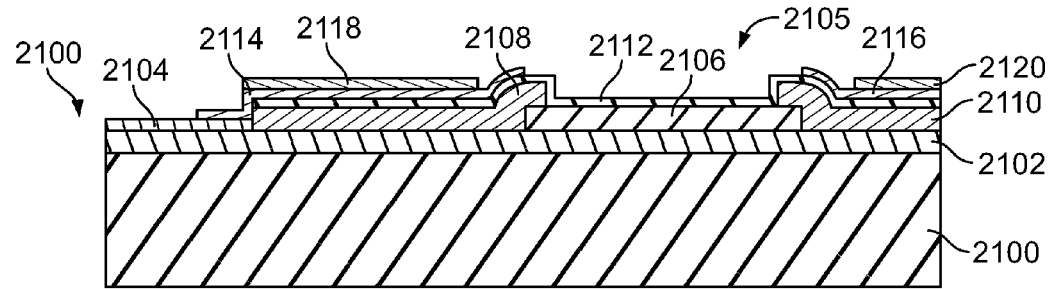

FIG. 21C shows that a first electrode layer 2114 (e.g., a deionizing or desalting electrode) and a second electrode layer 2116 (e.g., a deionizing or desalting electrode) are deposited on the sensor 2105. The first and second inter-layer dielectric insulators 2108, 2110 insulate the desalting electrodes. In this example, the first and second electrode layers 2114, 2116 are platinum. However, in other examples, the first and second electrode layers 2114, 2116 may comprise other suitable electrode material(s) such as, for example, gold, silver, silver chloride, titanium, etc. In some examples, the desalting electrodes 2114, 2116 are included using a two-layer combination of a lift-off resist and a positive tone thin photoresist. In other examples, other methods of depositing the electrodes are used.

The example system or apparatus, 2100 also includes a first oxide dielectric layer 2118 and a second oxide dielectric layer 2120, as shown in FIG. 21 D. In some examples, the dielectric layers 2118, 2120 include a layer of plasma-enhanced chemical vapor deposition (PECVD). In the illustrated examples, the first oxide dielectric layer 2118 is coupled to the first electrode 2114 and the second oxide dielectric layer 2120 is coupled to the second electrode 2116. In addition, in some examples, portion(s) of the oxide dielectric layers 2118, 2120 may be removed and/or patterns formed therein via a subtractive processing such as, for example, photolithography, wet-etching, etc. The removal of portion(s) of the dielectric layers 2128, 2120 exposes the first and second desalting electrodes 2114, 2116 in the sensing region around the gate 2106. In some examples, passivation occurs by use of the PECVD layers, which decreases the amount of surface area of the desalting electrodes 2114, 2116 in contact with the sample.

Figure 22:
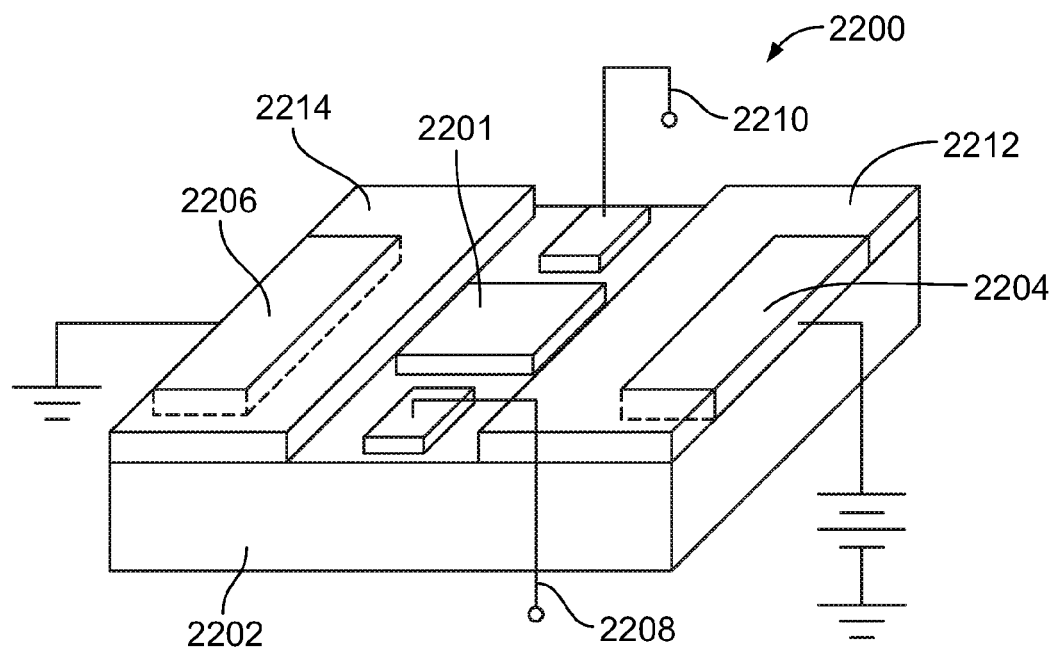
FIG. 22 is a perspective view of an example system or apparatus for desalting samples having example electrodes that are passivated.
Figure 23:
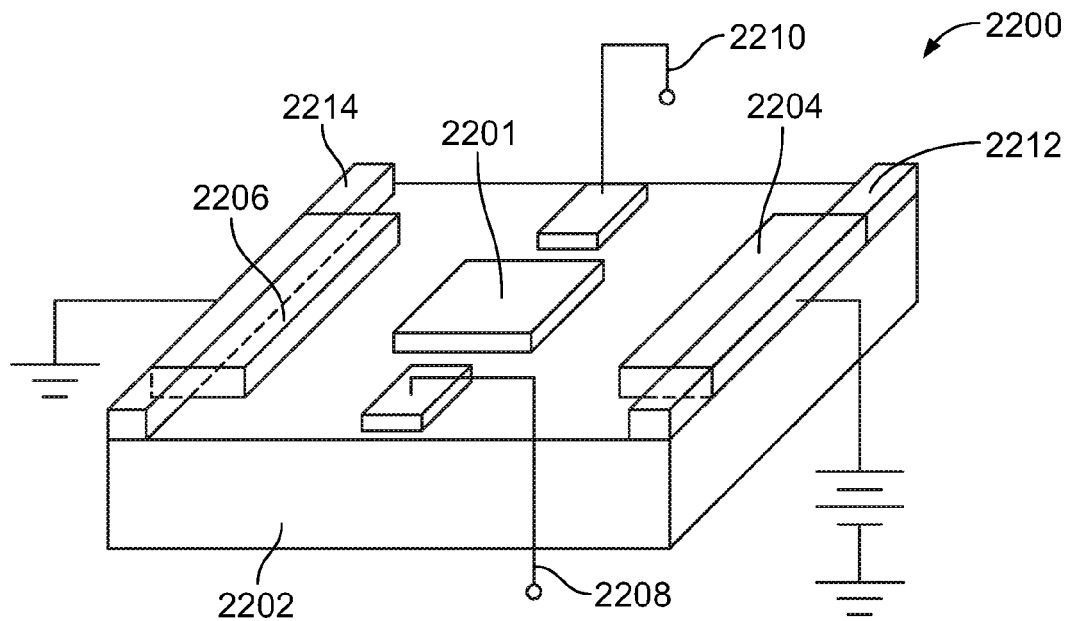
FIG. 23 is a perspective of the system or apparatus of FIG. 22 where the electrodes are substantially exposed.

FIGS. 22 and 23 are perspective views of an example system or apparatus for desalting samples 2200, which may be utilized, for example, by the system 300 of FIG. 3. The examples shown in FIGS. 22 and 23 illustrate example passivated and exposed desalting electrode configurations. In the example shown, a sensor 2201 is disposed on a substrate 2202 between a first desalting electrode 2204, a second desalting electrode 2206, a first sensing electrode 2208 and a second sensing electrode 2210. The first and second sensing electrodes 2208, 2210 may be used to measure the voltage and/or impedance occurring in the sample. However, in other examples, the first and second sending electrodes 2208, 2210 are desalting electrodes and are used to move ions away from the sensor 2201. The first and second desalting electrodes 2204, 2206 create an electric potential to move ions in the sample away from the surface of the sensor 2201. The length of the first and second desalting electrodes 2204, 2206 and the distance from the first and second desalting electrodes 2204, 2206 to the sensor 2200 affect the sensing behavior.

A passivated configuration, such as that shown in FIG. 22, includes a first passivation layer 2212 that covers by, for example, coating, encapsulating, shielding, etc. the first desalting electrode 2204. The example also includes a second passivation layer 2214 that covers the second desalting electrode 2206. The first and second passivation layers 2212, 2214 shield specific areas, portions, or sections of the first and second desalting electrodes 2204, 2206 from exposure to electrochemical activity within the sample solution so that only a small region of the sensor 2201 is exposed. In some examples, passivation is used to decrease the likelihood of a short circuit between the first and second desalting electrodes 2204, 2206.

In the example shown in FIG. 23, the first and second passivation layers 2212, 2214 are smaller and cover less of the first and second desalting electrodes 2204, 2206 than the example shown in FIG. 22. In this example, the first and second desalting electrodes 2204, 2206 are substantially more exposed to the sample and, thus, more surface area of the first and second desalting electrodes 2204, 2206 is exposed to move ions away from the sensor 2201.

In some examples, one or more of the electrode(s) and/or the sensor(s) described herein, may have a movable position that changes during and/or between application of electrical potentials. In some examples, the strength and/or duration of electric fields may be varied. In some examples, the type of electric field (e.g., DC, AC, DC and AC, etc.) may be varied. In some examples, the electrode material of one or more of the electrode(s) is varied. In some examples, the frequency and/or timing of an AC field and/or super-imposed DC field is varied. In some examples, one or more of the electrode(s) are embedded and/or coated with a dielectric to prevent (or accelerate) chemical reactions. The different multiple configurations and variants may be modified and/or combined in any suitable manner to optimize the electric fields.

In some examples, the sample solution of interest is a biological sample. In other examples, the solution of interest is a non-biological sample. In some examples, the sample solution includes blood, serum, plasma, and/or urine. In some examples, the biosensor detects proteins, antibodies, antigens, viruses, and/or nucleic acids. In other examples, the sensor detects a change in local pH, which, for example, is used in molecular (e.g., DNA) sensing.

While an example manner of implementing the desalting systems or apparatus 300, 400, 500, 900, 1000, 1400, 1600, 1700, 1900, 2000, 2100 and 2200 have been illustrated in FIGS. 3, 4A, 4B, 5, 7, 9-12 and 14-23 one or more of the elements, processes and/or devices illustrated in FIGS. 3, 4A, 4B, 5, 7, 9-12 and 14-23 may be combined, divided, re-arranged, omitted, eliminated and/or implemented in any other way. Further, the example processor may be implemented by hardware, software, firmware and/or any combination of hardware, software and/or firmware. Thus, for example, the example processor 302 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)), etc. When reading any of the apparatus or system claims of this patent to cover a purely software and/or firmware implementation, at least one of the example elements of any system disclosed herein (e.g., the example processor 302) is/are hereby expressly defined to include a tangible computer readable storage device or storage disk such as a memory, a digital versatile disk (DVD), a compact disk (CD), a Blu-ray disk, etc. storing the software and/or firmware. Further still, the example desalting systems or apparatus 300, 400, 500, 900, 1000, 1400, 1600, 1700, 1900, 2000, 2100 and 2200 of FIGS. 3, 4A, 4B, 5, 7, 9-12 and 14-23 may include one or more elements, processes and/or devices in addition to, or instead of, those illustrated in FIGS. 3, 4A, 4B, 5, 7, 9-12 and 14-23, and/or may include more than one of any or all of the illustrated elements, processes and devices.

A flowchart representative of example machine readable instructions for implementing the example desalting systems or apparatus 300, 400, 500, 900, 1000, 1400, 1600, 1700, 1900, 2000, 2100 and 2200 of FIGS. 3, 4A, 4B, 5, 7, 9-12 and 14-23. In this example, the machine readable instructions comprise a program for execution by a processor such as the processor 2512 shown in the example computer 2500 discussed below in connection with FIG. 25. The program may be embodied in software stored on a tangible computer readable medium such as a CD-ROM, a floppy disk, a hard drive, a digital versatile disk (DVD), a Blu-ray disk, or a memory associated with the processor 2512, but the entire program and/or parts thereof could alternatively be executed by a device other than the processor 2512 and/or embodied in firmware or dedicated hardware. Further, although the example program is described with reference to the flowchart illustrated in FIG. 24, many other methods of implementing the example desalting systems or apparatus 300, 400, 500, 900, 1000, 1400, 1600, 1700, 1900, 2000, 2100 and 2200 may alternatively be used. For example, the order of execution of the blocks may be changed, and/or some of the blocks described may be changed, eliminated, or combined.

As mentioned above, the example processes of FIG. 24 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 24 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 24:
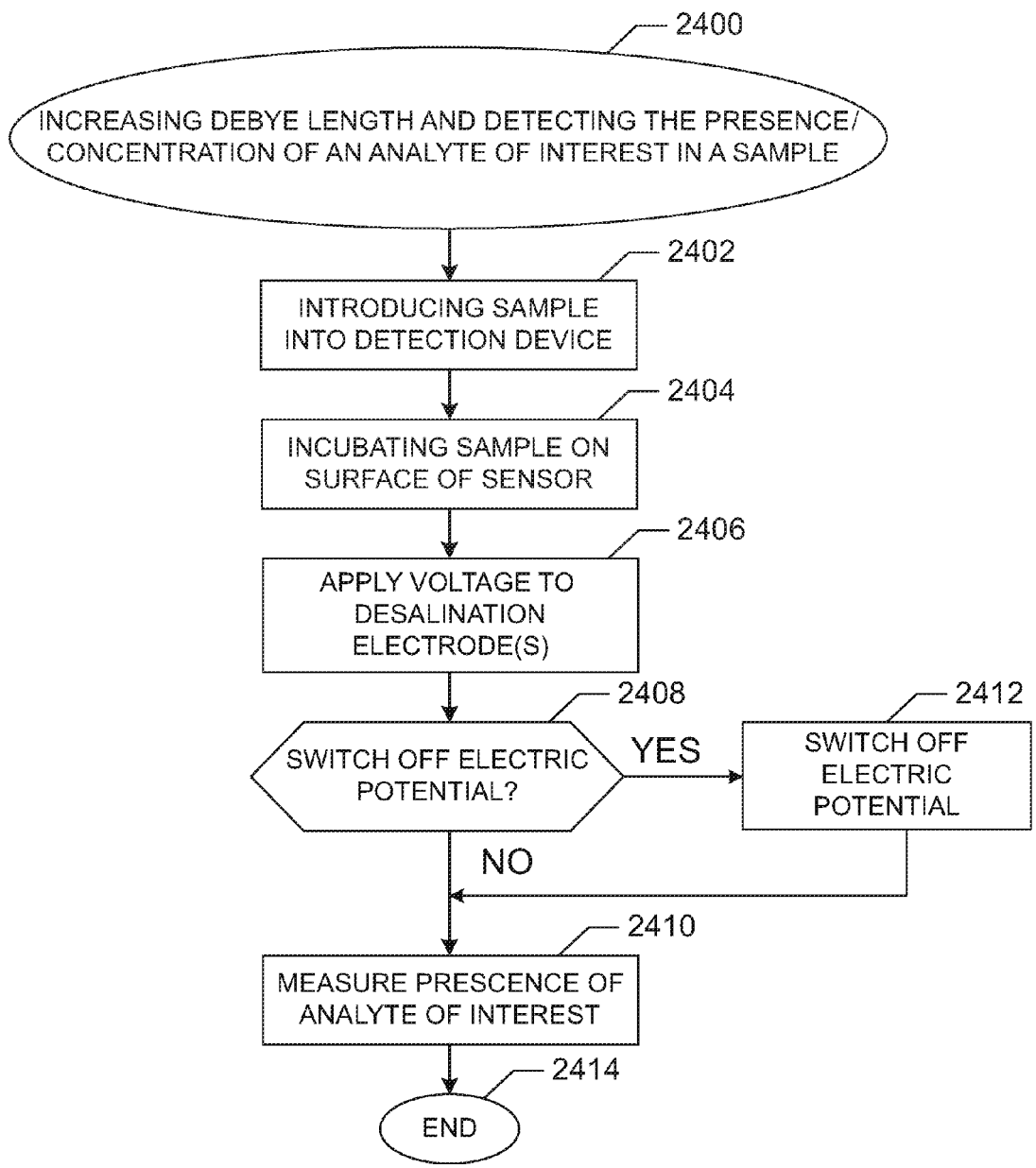
FIG. 24 is a flow chart representing an example method of desalting samples in accordance with the teachings of this disclosure.

An example method 2400 of increasing the Debye length and detecting the presence/concentration an analyte of interest in a sample is shown in FIG. 24. The example method 2400 may be, for example, performed by the processor 302, the sensors 304 and/or the electrodes 306 shown in FIG. 3. For example, as shown in FIG. 3, the processor 302 is communicatively coupled to the sensors 304 and the electrodes 306. The sensors 304 may be used to measure the concentration and/or presence of an analyte of interest in a sample fluid. The processor 302 may control the electrodes 306 to create an electric potential and attract ions in the sample away from the sensors 304 and towards the electrodes 306.

The example process 900 includes introducing a sample into a detection device (block 2402) that includes a sensor such as, for example, the example sensors 304, 401, 501, 901, 1001, 1401, 1601, 1701, 1904a-d, 2005, 2105 and/or 2201 disclosed above. The sample may be, for example, serum, blood, urine, etc. The sample may be manually loaded and/or, in some examples, automatically introduced to the detection device. In some examples, the sample is introduced to the detection device via a flow channel such as, for example, the flow channel shown in FIGS. 12, 16A and 16B. In other examples, the sample is stationary on the sensor (e.g., in a well).

The example process 2400 also includes incubating (block 2404). In some examples, the sample is incubated on a surface of a sensor (block 2404). In other examples, the example process 2400 continues without incubating the sample.

The example process 2400 also includes applying an electric potential or voltage (block 2406) via desalting electrodes. The electric potential may be applied, for example, during incubation and/or after incubation. In some examples, the electric potential may be produced from a source such as, for example, the desalting electrodes 306, 414, 514, 516, 914, 916, 1010, 1012, 1404, 1406, 1604, 1606, 1704-1710, 1906a-h, 2014, 2016, 2114, 2116, 2204 and/or 2206 disclosed above. The application of voltage attracts ions in the sample to the counter-charged desalting electrodes and moves the ions away from the surface of the detection device or sensor.

The example process 900 also includes determining whether to switch off or otherwise remove or discontinue the electric potential (block 2408). In some examples, the electrical potential may continue and the detection device measures the presence of the analyte of interest (block 2410). In other examples, the electric potential is stopped (block 2412) prior to measuring the presence of the analyte of interest (bock 2414). The analyte of interest may be measured using a sensor such as, for example, the sensors 304, 401, 501, 901, 1001, 1401, 1601, 1701, 1904a-d, 2005, 2105 and/or 2201 disclosed above.

The example process 2400 avoids eliminating the salt ions the bulk sample, unlike prior methods. Rather, with the example systems, apparatus and methods disclosed herein, the salt ions are repositioned. The Debye length at the sensor surface is increased due to the migration of the ions towards the electrodes.

Figure 25:
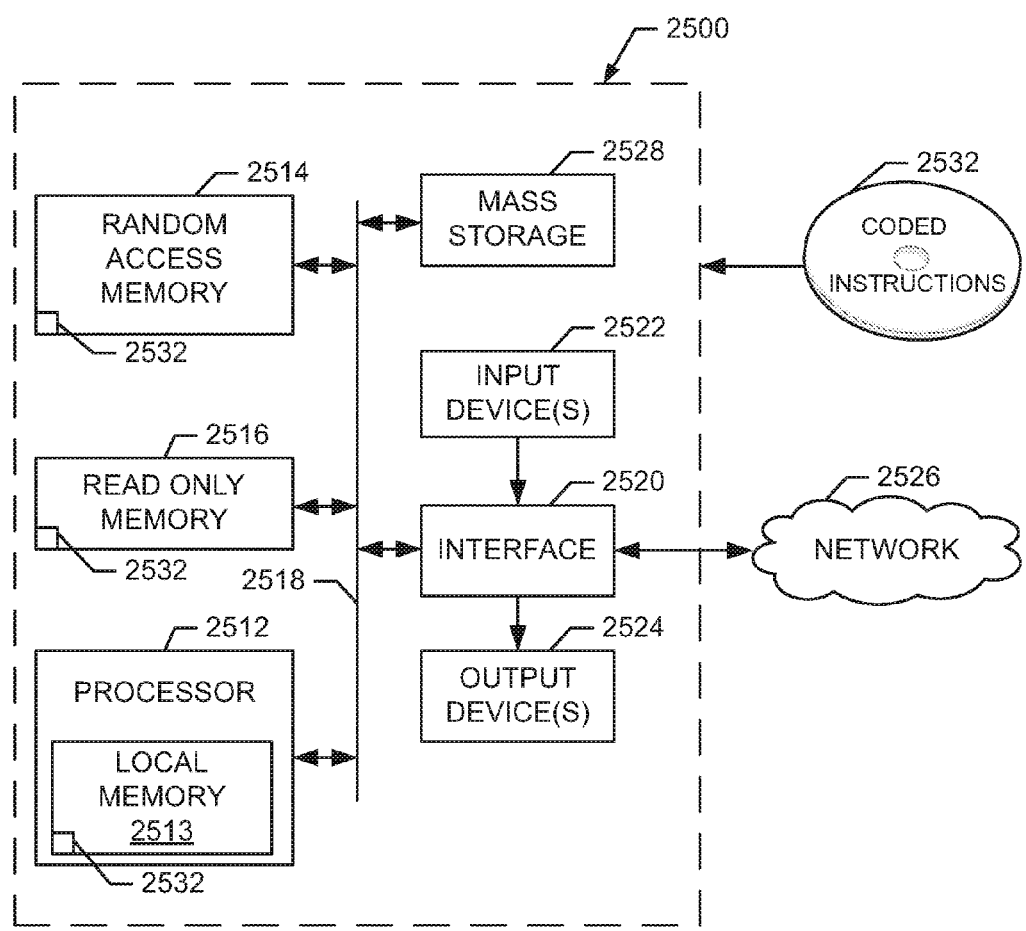
FIG. 25 illustrates an example processor platform that may be used to implement the example methods, systems and/or apparatus disclosed herein.

FIG. 25 is a block diagram of an example processor platform 2500 capable of executing the instructions of FIG. 24 to implement the example desalting systems and apparatus 300, 400, 500, 900, 1000, 1400, 1600, 1700, 1900, 2000, 2100 and 2200 of FIGS. 3, 4A, 4B, 5, 7, 9-12 and 14-23. The processor platform 2500 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player or any other type of computing device.

The processor platform 2500 of the illustrated example includes a processor 2512. The processor 2512 of the illustrated example is hardware. For example, the processor 2512 can be implemented by one or more integrated circuits, logic circuits, microprocessors or controllers from any desired family or manufacturer.

The processor 2512 of the illustrated example includes a local memory 2513 (e.g., a cache). The processor 2512 of the illustrated example is in communication with a main memory including a volatile memory 2514 and a non-volatile memory 2516 via a bus 2518. The volatile memory 2514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2516 may be implemented by flash memory and/or any other desired type of memory device. Access to the main memory 2514, 2516 is controlled by a memory controller.

The processor platform 2500 of the illustrated example also includes an interface circuit 2520. The interface circuit 2520 may be implemented by any type of interface standard, such as an Ethernet interface, a universal serial bus (USB), and/or a PCI express interface.

In the illustrated example, one or more input devices 2522 are connected to the interface circuit 2520. The input device(s) 2522 permit(s) a user to enter data and commands into the processor 2512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2524 are also connected to the interface circuit 2520 of the illustrated example. The output devices 2524 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 2520 of the illustrated example, thus, typically includes a graphics driver card, a graphics driver chip or a graphics driver processor.

The interface circuit 2520 of the illustrated example also includes a communication device such as a transmitter, a receiver, a transceiver, a modem and/or network interface card to facilitate exchange of data with external machines (e.g., computing devices of any kind) via a network 2526 (e.g., an Ethernet connection, a digital subscriber line (DSL), a telephone line, coaxial cable, a cellular telephone system, etc.).

The processor platform 2500 of the illustrated example also includes one or more mass storage devices 2528 for storing software and/or data. Examples of such mass storage devices 2528 include floppy disk drives, hard drive disks, compact disk drives, Blu-ray disk drives, RAID systems, and digital versatile disk (DVD) drives.

The coded instructions 2532 of FIG. 24 may be stored in the mass storage device 2528, in the volatile memory 2514, in the non-volatile memory 2516, and/or on a removable tangible computer readable storage medium such as a CD or DVD.

From the foregoing, it will appreciate that the above disclosed methods, apparatus and articles of manufacture provide a fast, passive methodology of mitigating the desensitizing effects of ions in solution.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A method comprising:
    introducing a sample into an apparatus, the apparatus including:
        a sensor coupled to a substrate; and
        an electrode; and
    applying, via the electrode, an electric potential to the sample to redistribute ions in the sample relative to the sensor.

2. The method of claim 1 further including moving the ions away from the sensor using the electric potential.

3. The method of claim 2, wherein moving the ions away from the sensor increases a Debye length of the sample.

4. The method of claim 2 further comprising desalting the sample by moving the ions away from the sensor, wherein the ions are salt ions.

5. The method of claim 1 further including detecting, with the sensor, a presence of an analyte in the sample.

6. The method of claim 5, wherein detecting the presence of the analyte includes measuring a change in at least one of a resistance, a current, a capacitance, an impedance or a voltage across the sensor.

7. The method of claim 5 further including discontinuing the electric potential prior to detecting the presence of the analyte in the sample.

8. The method of claim 5, wherein the sensor includes a field-effect transistor having a gate.

9. The method of claim 8, wherein the gate is functionalized with a binding agent to interact with the analyte.

10. The method of claim 9, wherein the gate includes a nanowire.

11. The method of claim 1, wherein the electrode is a first electrode, the apparatus further including a second electrode, and wherein the first electrode and the second electrode create the electric potential to redistribute the ions.

12. The method of claim 11, wherein the first electrode and the second electrode are coupled to the substrate, and the sensor is located between the first electrode and the second electrode.

13. The method of claim 12, wherein the first electrode and the second electrode are substantially coplanar with the sensor on the substrate.

14. The method of claim 11, wherein the first electrode is a first desalting electrode and the second electrode is a second desalting electrode, and wherein the sensor includes a field-effect transistor having a source electrode, a drain electrode and a gate.

15. The method of claim 14, wherein the first desalting electrode, the source electrode, the drain electrode and the second desalting electrode are in a linear arrangement with the gate.

16. The method of claim 11, wherein applying the electric potential includes applying a positive electric voltage with the first electrode and applying a negative electric voltage with the second electrode.

17. The method of claim 11, wherein the apparatus further includes a third electrode and a fourth electrode coupled the substrate, the first electrode, the second electrode, the third electrode and the fourth electrode being disposed on each of four sides around the sensor.

18. The method of claim 1, wherein the sample is a raw sample and does not contain a buffer solution of ionic concentration.

* * * * *